(12) United States Patent
Gerke et al.

(10) Patent No.: US 11,986,518 B2
(45) Date of Patent: May 21, 2024

(54) IMMUNOGENIC COMPOSITIONS

(71) Applicant: GLAXOSMITHKLINE BIOLOGICALS SA, Rixensart (BE)

(72) Inventors: Christiane Gerke, Siena (IT); Laura Bartle Martin, Siena (IT); Allan James Saul, Siena (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 16/985,979

(22) Filed: Aug. 5, 2020

(65) Prior Publication Data
US 2020/0384096 A1   Dec. 10, 2020

Related U.S. Application Data

(62) Division of application No. 15/736,691, filed as application No. PCT/EP2016/063776 on Jun. 15, 2016, now abandoned.

(30) Foreign Application Priority Data

Jun. 16, 2015   (EP) ..................................... 15020097

(51) Int. Cl.
*A61K 39/112*   (2006.01)
*A61K 39/00*   (2006.01)

(52) U.S. Cl.
CPC ............. *A61K 39/0283* (2013.01); *A61K 2039/55505* (2013.01); *A61K 2039/55572* (2013.01); *A61K 2039/70* (2013.01); *Y02A 50/30* (2018.01)

(58) Field of Classification Search
CPC ...... A61K 39/0283; A61K 2039/55505; A61K 2039/55572; A61K 2039/70; Y02A 50/30
See application file for complete search history.

(56) References Cited

U.S. PATENT DOCUMENTS

| | | | |
|---|---|---|---|
| 5,681,736 A | 10/1997 | Pace et al. | |
| 10,485,861 B2 * | 11/2019 | Stary | A61K 31/711 |
| 10,500,263 B2 * | 12/2019 | Porro | A61K 39/107 |
| 11,339,367 B2 * | 5/2022 | Gerke | A61P 31/04 |
| 2013/0052227 A1 * | 2/2013 | Gerke | A61P 1/00 424/234.1 |
| 2016/0289632 A1 * | 10/2016 | Gerke | A61P 31/04 |
| 2018/0169206 A1 * | 6/2018 | Gerke | A61P 31/04 |

(Continued)

FOREIGN PATENT DOCUMENTS

| | | |
|---|---|---|
| CN | 103933559 A | 7/2014 |
| CN | 103966308 B | 4/2016 |
| EP | 3310381 A1 * | 4/2018 ......... A61K 39/0283 |

(Continued)

OTHER PUBLICATIONS

Mancini et al Frontiers in Immunology. Aug. 2021. vol. 12. Article 715393. 7 pages. published: Aug. 3, 2021 (Year: 2021).*

(Continued)

*Primary Examiner* — Gary B Nickol
*Assistant Examiner* — Amelia Nicole Dickens
(74) *Attorney, Agent, or Firm* — LOZA & LOZA, LLP; Julio Loza; Jayshree Gerken

(57) ABSTRACT

This invention relates to immunogenic compositions, particularly vaccine compositions, for use in providing protection against illness caused by bacterial infection with *Shigella* strains.

12 Claims, 7 Drawing Sheets

Specification includes a Sequence Listing.

(56) References Cited

U.S. PATENT DOCUMENTS

| | | | | |
|---|---|---|---|---|
| 2020/0215179 A1* | 7/2020 | Stary | .................... | A61K 39/092 |
| 2020/0384096 A1* | 12/2020 | Gerke | .................... | A61P 37/02 |

FOREIGN PATENT DOCUMENTS

| | | | | |
|---|---|---|---|---|
| WO | 2011036564 A | 3/2011 | | |
| WO | WO-2011036564 A2 * | 3/2011 | ............. | A61K 39/00 |
| WO | 2012/049662 A1 | 4/2012 | | |
| WO | 2014/192031 A1 | 12/2014 | | |
| WO | WO-2014192031 A1 * | 12/2014 | ......... | A61K 39/0283 |
| WO | 2016202872 A1 | 12/2016 | | |
| WO | WO-2016202872 A1 * | 12/2016 | ......... | A61K 39/0283 |
| WO | 2018096013 A1 | 5/2018 | | |

OTHER PUBLICATIONS

Thompspn et al, Vaccine, 2016. 34:783-790. available online: Dec. 29, 2015 (Year: 2016).*

Tondi et al, Frontiers in Cellular and Infection Microbiology. Feb. 2022. vol. 12. Article 767153. 10 pages. published: Feb. 3, 2022 (Year: 2022).*

Van de Waterbeemd et al. "Improved OMV vaccine against Neisseria meningitidis using genetically engineered strains and a detergent-free purification process", May 16, 2010, Vaccine, vol. 28, p. 4810-4816. (Year: 2010).*

Van der Pol et al. "Outer membrane vesicles as platform vaccine technology", Nov. 11, 2015, Biotechnology Journal, vol. 10, p. 1689-1706. (Year: 2015).*

Livio et al, "Shigella Isolates From the Global Enteric Multicenter Study Inform Vaccine Development", Clinical Infectious Diseases, vol. 59, No. 7, 2014, pp. 933-941—Originally cited in IDS filed Aug. 5, 2020. (Year: 2014).*

Kotloff KL, Nataro JP, Blackwelder WC, Nasrin D, Farag TH, Panchalingam S, et al. Burden and aetiology of diarrhoeal disease in infants and young children in developing countries (the Global Enteric Multicenter Study, GEMS): a prospective, case-control study. Lancet. 2013;382: 209-222. (Year: 2013).*

Kotloff et al. "Safety, Immunogenicity, and Transmissibility in humans of CVD 1203, a live oral Shigella flexneri 2a vaccine candidate attenuated by deletions in aroA and virG". Nov. 1996, Infection and Immunity, vol. 64 No. 11, p. 4542-4548. (Year: 1996).*

Liu et al. (2020), Live attenuated Salmonella Typhimurium with monophosphoryl lipid A retains ability to induce T-cell and humoral immune responses against heterologous polysaccharide of Shigella flexneri 2a. Int. J. Med. Microbiol. 310(5): 151427. (Year: 2020).*

Liu et al. "Structure and genetics of Shigella O antigens", Apr. 17, 2008, FEMS Microbiol Rev, vol. 32, p. 627-653. (Year: 2008).*

Scorza et al, "High Yield Production Process for Shigella Outer Membrane Particles", PLOS ONE, vol. 7, No. 6, 2012, p. e35616; 15 total pages.

Livio et al, "Shigella Isolates From the Global Enteric Multicenter Study Inform Vaccine Development", Clinical Infectious Diseases, vol. 59, No. 7, 2014, pp. 933-941.

Soma Mitra et al, "Multi-serotype outer membrane vesicles of Shigellae confer passive protection to the neonatal mice against shigellosis", Vaccine, Elsevier Ltd, GB, vol. 31, 2013, pp. 3163-3173.

Rossi et al, "Modulation of Endotoxicity of Shigella Generalized Modules for Membrane Antigens (GMMA) by Genetic Lipid A Modifications: Relative Activation of TLR4 and TLR2 Pathways in Different Mutants", Journal of Biological Chemistry, vol. 289, No. 36, 2014, pp. 24922-24935.

Marie-Laure Rosso, "Periodic Report Summary 1—Stopenterics (Vaccination against Shigella and ETEC: novel antigens, novel approaches)", St Opent Erics Report Summary, Jan. 18, 2013 (Jan. 18, 2013); 4 total pages.

Marie-Laure Rosso, "Periodic Report Summary 2—Stopenterics (Vaccination against Shigella and ETEC: Novel antigens, novel approaches)", St Opent Erics Report Summary, Jun. 12, 2013 (Jun. 12, 2013); 5 total pages.

International Search Report and Written Opinion for International Application No. PCT/EP2016/063776 dated Aug. 10, 2016; 12 total pages.

Gerke et al, PLoSONE. Aug. 6, 2015, 10/8:e0134478, 23 pages. published: Aug. 6, 2015 (Year: 2015).

Gerke et al, Am. J. Trap. Med. and Hyg., Nov. 2012, 87/5, Suppl 1, . . . 320. Abstract No. 1050 (abstract only) (Year: 2012).

Maggiore et al, International J. Medical Microbiology. Feb. 1, 2016. 306/2:99-108. (abstract only) (Year: 2016).

Rossi et al, Mol. Biotechnol., 2015, 57:84-93. Published online: Sep. 16, 2014. (Year: 2015).

D'Hauteville Helene et al: "Two msbB genes encoding maximal acylation of lipid A are required for invasive Shigella flexneri to mediate inflammatory rupture and destruction of the intestinal epithelium", The Journal of Immunology, Williams & Wilkins Co, US, vol. 168, No. 10, May 15, 2002 (May 15, 2002), pp. 5240-5251, XP002463186.

EP Patent Office, Summons to attend oral proceedings, Jun. 13, 2022, 12 pages.

Noriega FR et al. (1999), Strategy for cross-protection among Shigella flexneri serotypes. Infect. Immun. 67 (2):782-788.

Karnell et al. (1992), Auxotrophic live oral Shigella flexneri vaccine protects monkeys against challenge with S. flexneri of different serotypes. Vaccine 10(3):167-174.

Jennison et al. (2004), Shigella flexneri infection: pathogenesis and vaccine development. FEMS Microbiol. Rev. 28 (1):43-58.

Perepelov AV et al. (2012), Shigella flexneri O-antigens revisited: final elucidation of the O-acetylation profiles and a survey of the O-antigen structure diversity. FEMS Immunol. Med. Microbiol. 66(2):201-210. Abstract only.

Vulliez-Le Normand B et al. (2008), Structures of synthetic O-antigen fragments from serotype 2a Shigella flexneri in complex with a protective monoclonal antibody. PNAS, 105(29):9976-9981.

Ledov Vladimir A et al. (2019), Highly homogenous tri-acylated S-LPS acts as a novel clinically applicable vaccine against Shigella flexneri 2a infection. Vaccine 37(8):1062-1072.

Liu et al. (2020), Live attenuated Salmonella Typhimurium with monophosphoryl lipid A retains ability to induce T-cell and humoral immune responses against heterologous polysaccharide of Shigella flexneri 2a. Int. J. Med. Microbiol. 310(5):151427.

Barnoy S et al. (2009), Characterization of WRSs2 and WRSs3, new second-generation virG(icsA)-based Shigella sonnei vaccine candidates with the potential for reduced reactogenicity. Vaccine 28(6): 1642-1654.

Kotloff KL, Nataro JP, Blackwelder WC, Nasrin D, Farag TH, Panchalingam S, et al. Burden and aetiology of diarrhoeal disease in infants and young children in developing countries (the Global Enteric Multicenter Study, GEMS): a prospective, case-control study. Lancet. 2013;382: 209-222.

Erlandson, A.L., & Mackey, W.H. Growth and Manometric Studies on Carbohydate Utilization by Shigella Flexneri.J Bacteriol 1958; 75(3): 253-7.

Robbins JB, Kubler-Kielb J, Vinogradov E, Mocca C, Pozsgay V, Shiloach J, et al. Synthesis, characterization, and immunogenicity in mice of Shigella sonnei O-specific oligosaccharide-core-protein conjugates. Proc Natl Acad Sci U S A. 2009;106: 7974-7978.

Rossi O, Maggiore L, Necchi F, Koeberling O, MacLennan CA, Saul A, Gerke C. Comparison of colorimetric assays with quantitative amino acid analysis for protein quantification of Generalized Modules for Membrane Antigens (GMMA). Mol Biotechnol. Jan. 2015;57(1):84-93.

Datsenko, K. A., & Wanner, B. L. (2000). One-step inactivation of chromosomal genes in *Escherichia coli* K-12 using PCR products. Proceedings of the National Academy of Sciences of the United States of America, 97(12), 6640-6645.

International Search Report dated Dec. 7, 2022, for Application No. PCT/EP2022/073501, 21 pages.

International Search Report dated Jan. 22, 2021, for Application No. PCT/EP2020079140, 15 pages.

(56) References Cited

OTHER PUBLICATIONS

European Search Report dated Jul. 24, 2020, for Application No. EP19203834, 6 pages.
Great Britain Search Report dated Apr. 29, 2022, for Application No. GB2112149.6, 2 pages.
Murray CJ, Vos T, Lozano R, Naghavi M, Flaxman AD, Michaud C, et al. Disability-adjusted life years (DALYs) for 291 diseases and injuries in 21 regions, 1990-2010: a systematic analysis for the Global Burden of Disease Study 2010. Lancet. 2012;380: 2197-2223.
Lozano R, Naghavi M, Foreman K, Lim S, Shibuya K, Aboyans V, et al. Global and regional mortality from 235 causes of death for 20 age groups in 1990 and 2010: a systematic analysis for the Global Burden of Disease Study 2010. Lancet. 2012;380: 2095-2128.
Levine MM, Kotloff KL, Barry EM, Pasetti MF, Sztein MB. Clinical trials of Shigella vaccines: two steps forward and one step back on a long, hard road. Nat Rev Microbiol. 2007;5: 540-553.
Chang Z, Lu S, Chen L, Jin Q, Yang J. Causative species and serotypes of shigellosis in mainland China: systematic review and meta-analysis. PLOS One. 2012;7: e52515.
Vinh H, Nhu NTK, Nga TVT, Duy PT, Campbell JI, Hoang NVM, et al. A changing picture of shigellosis in southern Vietnam: shifting species dominance, antimicrobial susceptibility and clinical presentation. BMC Infect Dis. 2009;9: 204.
Kweon, M-N. Shigellosis: the current status of vaccine development. 2008 Curr Opin Infect Dis. 21(3):313-8.
Cohen D, Ashkenazi S, Green MS, Gdalevich M, Robin G, Slepon R, et al. Double-blind vaccine-controlled randomised efficacy trial of an investigational Shigella sonnei conjugate vaccine in young adults. Lancet. 1997;349: 155-159.
Passwell JH, Ashkenzi S, Banet-Levi Y, Ramon-Saraf R, Farzam N, Lerner-Geva L, et al. Age-related efficacy of Shigella O-specific polysaccharide conjugates in 1-4-year-old Israeli children. Vaccine. 2010;28: 2231-2235.
Susanna Esposito , Roman Prymula , Gian Vincenzo Zuccotti , Fang Xie , Michelangelo Barone , Peter M Dull , Daniela Toneatto, A phase II randomized controlled trial of a multicomponent meningococcal serogroup B vaccine, 4CMenB, in infants (II). Human Vaccines & Immunotherapeutics vol. 10, Iss. 7, 2014.
Uyttendaele M, Bagamboula CF, De Smet E, Van Wilder S, Debevere J. Evaluation of culture media for enrichment and isolation of Shigella sonnei and S. flexneri. Int J Food Microbiol. Nov. 8, 2001;70(3):255-65.

Formal SB, Kent TH, May HC, Palmer A, Falkow S, LaBrec EH. Protection of monkeys against experimental shigellosis with a living attenuated oral polyvalent dysentery vaccine. J Bacteriol. 1966;92: 17-22.
Makino S, Sasakawa C, Kamata K, Kurata T, Yoshikawa M. A genetic determinant required for continuous reinfection of adjacent cells on large plasmid in S. flexneri 2a. Cell. 1986;46: 551-555.
Prunier A-L, Schuch R, Fernandez RE, Mumy KL, Kohler H, McCormick BA, et al. nadA and nadB of Shigella flexneri 5a are antivirulence loci responsible for the synthesis of quinolinate, a small molecule inhibitor of Shigella pathogenicity. Microbiology. 2007;153: 2363-2372.
Clementz T, Bednarski JJ, Raetz CR. Function of the htrB high temperature requirement gene of *Escherichia coli* in the acylation of lipid A. J Biol Chem. 1996;271: 12095-12102.
Micoli F, Rondini S, Gavini M, Pisoni I, Lanzilao L, Colucci AM, et al. A scalable method for O-antigen purification applied to various Salmonella serovars. Anal Biochem. 2013;434: 136-145.
Stoddard MB, Pinto V, Keiser PB, Zollinger W. Evaluation of a whole-blood cytokine release assay for use in measuring endotoxin activity of group B Neisseria meningitidis vaccines made from lipid A acylation mutants. Clin Vaccine Immunol. 2010;17: 98-107.
Moscardo E, Maurin A, Dorigatti R, Champeroux P, Richard S. An optimised methodology for the neurobehavioural assessment in rodents. J Pharmacol Toxicol Methods. 2007;56: 239-255.
Jiang Y, Yang F, Zhang X, Yang J, Chen L, Yan Y, et al. The complete sequence and analysis of the large virulence plasmid pSS of Shigella sonnei. Plasmid. 2005;54: 149-159.
Zhu D, Huang S, Gebregeorgis E, Mcclellan H, Dai W, Miller L, Saul A. Development of a Direct ALHYDROGEL®Formulation Immunoassay (Dafia). J Immunol Methods. May 15, 2009;344(1):73-8.
Wu Chenglong, Yang Zhong, "Study on the expression of Shigella flexneri antigen gene in Salmonella typhi oral vaccine Ty21a strain", Chinese Journal of Guizhou Medicine, 1996; 20(1).
L. S. Baron, et al., Introduction of Shigella flexneri 2a Type and Group Antigen Genes into Oral Typhoid Vaccine Strain Salmonella typhi Ty2la, Infection and Immunity, Nov. 1987, p. 2797-2801.
Maggiore, Luana, Membrane particles as Shigella vaccine candidate: generation, proteomic and immunoproteomic analysis / doctoral teshis—(Jan. 27, 2012), Universidad de Padova. https://hdl.handle.net/11577/3422054.
Argentinian Office Action dated Dec. 22, 2023 for application No. 20160101784, 8 pages.

* cited by examiner

A

B

IMMUNOGENIC COMPOSITIONS

REFERENCE TO SEQUENCE LISTING SUBMITTED ELECTRONICALLY VIA EFS-WEB

The contents of the electronically submitted sequence listing (Name: VN56961_US_sequence_listing.txt; 12,830 bytes; and Date of Creation: Jun. 16, 2015) was originally submitted in the International Application No. PCT/EP2016/063776, filed Jun. 16, 2015, and is incorporated herein by reference in its entirety.

TECHNICAL FIELD

This invention relates to immunogenic compositions, particularly vaccine compositions, for use in providing protection against illness caused by bacterial infection with *Shigella* strains.

BACKGROUND TO THE INVENTION

Shigellosis is a major global health problem, responsible for more than 7 million Disability-Adjusted Life Years and 100,000 deaths per year, especially in children under 5 years old in developing countries [1,2,3]. Shigellosis is caused by Gram-negative bacteria of the genus *Shigella*, which is divided into 4 species and further differentiated into 50 serotypes based on the structure and composition of the outer polysaccharide antigen (O antigen, OAg) of the lipopolysaccharide (LPS): *S. sonnei* (1 serotype), *S. flexneri* (15 serotypes), *S. boydii* (19 serotypes) and *S. dysenteriae* (15 serotypes) [4]. A limited number of serotypes contribute to the global burden of disease and these vary between regions and over time [4,5,6,7]. *Shigella sonnei* and *Shigella flexneri* 2a are the currently dominant serotypes worldwide [4,6].

The hallmark of clinical shigellosis is an acute rectocolitis associated with fever, nausea, anorexia, dehydration, mucopurulent and bloody diarrhea, and tenesmus. *Shigella*-caused dysentery is endemic and causes millions of illness episodes in developing countries. For example, there are estimated to be 125 million cases of *Shigella* diarrhea per year, 99% of which occur in developing countries and 69% of which occur in children under five years of age. The morbidity and mortality due to shigellosis are especially high among children in developing countries.

Existing approaches to *Shigella* vaccines (reviewed in [8]) have been based on live attenuated strains for oral immunisation, conjugated O saccharides for injection, proteosomes (meningococcal outer membrane vesicles with attached *Shigella* LPS) for intranasal use, invaplexes (sub-cellular extracts of *Shigella* including IpaB, IpaC and LPS) for intranasal use, and nuclear protein-ribosomal complexes prepared from ΔmsbB strains with detoxified LPS. Although two of these vaccines have been efficacious in field trials, none protects against multiple *Shigella* serotypes.

The most successful recent vaccine candidate, a parenteral *S. sonnei* OAg conjugate, showed 74% protection against homologous *S. sonnei* infection in young adults after one immunization [9] and 71% efficacy in children older than 3 years after two immunizations [10]. In contrast, the vaccine showed low immunogenicity and lack of protection in childrenyounger than 3 years [10]. The level of protection paralleled the level of the OAg vaccine-specific antibody response, measured as antibody response to *S. sonnei* LPS with the homologous OAg (anti-LPS response) [10].

Thus, it is an object of the invention to provide improved immunogenic compositions, particularly vaccine compositions that can be used to protect against multiple serotypes of *Shigella*. More particularly, it is an object to provide vaccine compositions that generate stronger responses to the OAg, especially in young children.

BRIEF DESCRIPTION OF THE INVENTION

In a first aspect the invention provides an immunogenic composition comprising Generalised Modules for Membrane Antigens (GMMA) purified from *Shigella sonnei* and *Shigella flexneri*. Particularly the GMMA comprise a modified lipid A. Particularly the modified lipid A is a less toxic or detoxified form of lipid A, by way of non-limiting example, a penta-acylated lipid A, a non-naturally occurring hexa-acylated lipid A wherein one of the acyl groups is substituted and/or a hexa-acylated lipid A wherein the lauroyl-chain is replaced by a palmitoleoyl chain. Yet more particularly, at least 75% of the *Shigella sonnei* GMMA have a diameter in the range of 25 nm to 40 nm as determined by electron microscopy. The *Shigella sonnei* GMMA may have an average radius in the range of 32 nm to 38 nm (determined by HPLC-SEC MALLS) and the *S. flexneri* GMMA may have an average radius (HPLC-SEC MALLS) of between 21 nm to 28 nm. In one embodiment, the *Shigella flexneri* GMMA are purified from at least one strain selected from the group consisting of 2a, 3a and 6. Particularly, the immunogenic composition comprises *Shigella flexneri* GMMA purified from each of strains 2a, 3a and 6. In one embodiment, the immunogenic composition comprises GMMA purified from (a) *Shigella sonnei*, (b) *Shigella flexneri* 2a, (c) *Shigella flexneri* 3a and (d) *Shigella flexneri* 6. Particularly the GMMA are present in a ratio of 1:1:1:1. Yet more particularly, the immunogenic composition comprises GMMA protein at a concentration of less than 100 µg/mL. Particularly the immunogenic composition comprises *Shigella flexneri* GMMA purified from each of strains 2a, 3a and 6 and GMMA purified from at least one further *Shigella flexneri* strain selected from the group consisting of 1b and 2b strains. Particularly, the immunogenic composition comprises GMMA purified from (a) *Shigella sonnei* ΔtolR, ΔhtrB, virG::nadAB, (b) *Shigella flexneri* 2a ΔtolR, ΔmsbB, (c) *Shigella flexneri* 3a ΔtolR, ΔmsbB and (d) *Shigella flexneri* 6 ΔtolR, ΔmsbB or ΔhtrB. Yet more particularly, the *Shigella flexneri* strain(s) are cured of the virulence plasmid. The composition may also contain GMMA of other *S. flexneri* strains.

Particularly, the immunogenic composition comprises an adjuvant. Yet more particularly, the adjuvant is an adsorbent. Still yet more particularly, the adjuvant is an adsorbent that does not enhance immunogenicity of GMMA, for example, as measured by anti-LPS antibody response. Particular adjuvants include, for example, aluminium adjuvants including aluminium hydroxide, ALHYDROGEL®, aluminium phosphate, potassium aluminium sulphate and alum.

In a second aspect, the invention provides a method for immunising a patient against infection by *Shigella* comprising the step of administering to the patient an immunogenic composition of the first aspect of the invention.

In a third aspect, the invention provides a composition of the first aspect of the inventions for use in a method of immunising a patient against infection by *Shigella*.

DETAILED DESCRIPTION OF THE INVENTION

Figure 1:
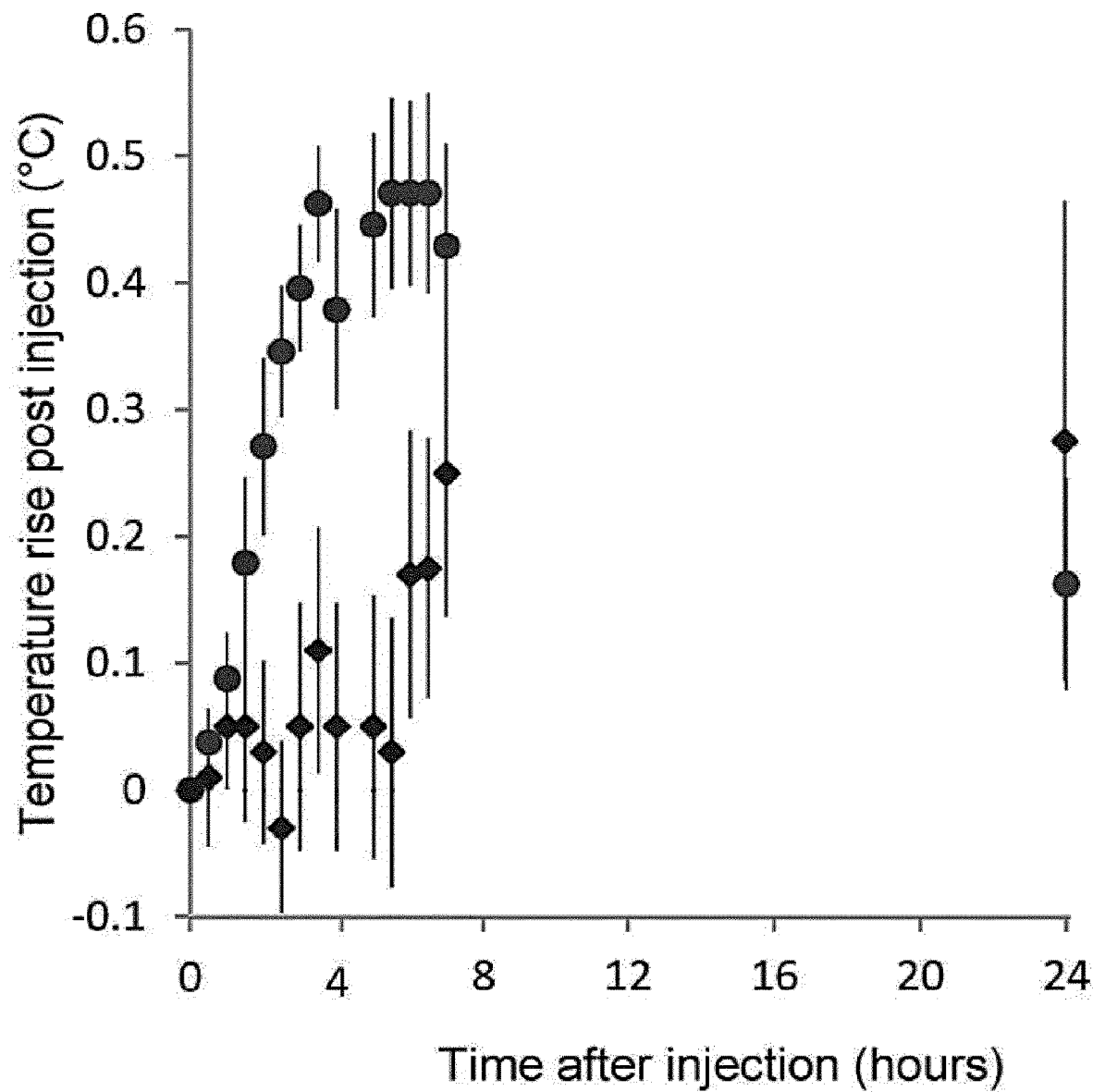
FIG. 1: Mean temperature rise (mean of post vaccination—pre-vaccination temperature) in rabbits after an IM injection of 100 µg protein containing dose of 1790GAHB (circles) or equivalent volume of physiological saline (diamonds). The vertical bars show the standard error of the mean. N=12 for the 1790GAHB and 6 for the saline injected rabbits.

Generalised Modules for Membrane Antigens or GMMA are particles derived from the outer membrane of Gram-negative bacteria that have high levels of LPS, lipoproteins, proteins and other antigens that activate the innate immune response. GMMA are produced from genetically-modified bacterial strains that are mutated to enhance vesicle production and to remove or modify antigens (e.g. lipid A). Enhanced spontaneous generation of vesicles can be achieved, for example, by targeted deletion of proteins involved in maintenance of membrane integrity (see below). The outer surface of GMMA corresponds to the outer surface of the bacterium from which they are derived, preserving all membrane antigens (including e.g. lipopoly-saccharides, lipooligosaccharides, lipoproteins, proteins) in the context of the membrane. GMMA (unlike detergent-extracted OMVs) retain these outer membrane components in their native conformation and correct orientation, better preserving immunogenicity against the bacterial strain from which they are derived. Thus, GMMA are highly immunogenic and this strong activation of innate immunity may lead to unacceptable reactions in human subjects, e.g. a febrile response or, in extreme cases, septic shock especially if parenterally administered.

The invention is based on the finding that genetic manipulation can be used to provide *Shigella* bacterial strains that produce GMMA that are immunogenic, even at low doses, with a reduced risk of, for example, pyrogenicity. The inventors have also discovered that the use of an aluminium adjuvant is advantageous in increasing in-vivo tolerability of immunogenic compositions comprising GMMA, further reducing the risk of, for example, pyrogenicity. As a result, doses of GMMA purified from multiple *Shigella* bacterial strains can be combined to prepare a multivalent immunogenic composition having a total GMMA protein concentration per dose of up to 100 µg/ml or higher. This finding is surprising because, in the literature, studies have generally investigated reducing the OMV content to avoid fever which could compromise the acceptability of detergent-derived OMV containing vaccines in infant vaccination schedules. For example, in studies of the 4CMenB vaccine, Bexsero, approximately half the subjects were observed to experience a temperature of ≥38.5° C. after vaccination with the first dose [11]. In contrast, the clinical trial data provided in the examples herein demonstrate that vaccination with an immunogenic composition comprising 100 µg/ml of *S. sonnei* GMMA (four times the equivalent content of OMV in 4CMenB) was well tolerated. Data in humans is supported by immunogenicity results generated in mice and rabbits.

The *Shigella* Bacterium

The invention is based on the use of *Shigella* bacteria selected from one or more of the serogroups *S. dysenteriae*, *S. flexneri*, *S. boydii* and *S. sonnei*. Particularly, the invention is based on the use of at least two strains of *Shigella* selected from serogroups *S. flexneri* and *S. sonnei*, particularly selected from the group consisting of *S. sonnei*, *S. flexneri* 2a, *S. flexneri* 3a and *S. flexneri* 6. In certain embodiments *S. sonnei* 53G, *S. flexneri* 1b STANSFIELD, *S. flexneri* 2a 2457T, *S. flexneri* 2b 69/50, *S. flexneria* 3a 6885 and or *S. flexneri* 6 10.8537 may be used.

Particularly, *Shigella* strains for use in the invention are ΔtolR strains having a disrupted Tol-Pal system which causes the bacterium to release greater quantities of GMMA into the culture medium during bacterial replication. The deletion of other genes in the Tol-Pal complex (eg, TolA) could also be envisaged, for example, as disclosed in WO 2011/036564.

*Shigella* strains for use in the invention include one or more further changes relative to a wild-type strain. Particularly, strains for use with the invention include one or more mutations resulting in inactivation of htrB, msbB1 and/or msbB2. By way of non-limiting example, suitable mutations may be selected from the group consisting of ΔhtrB, ΔmsbB1 and ΔmsbB2. For simplicity, double deletions of both msbB1 and msbB2 may also be referred to as ΔDmsbB. Inactivation of htrB or msbB1 and msbB2 reduce acylation in lipid A. In some embodiments, strains for use with the invention lack the O antigen in the LPS, thereby avoiding serotype-specific responses. In *S. sonnei* the O antigen is absent when the virulence plasmid is removed. In other embodiments, strains for use with the invention produce LPS comprising the O antigen. The presence of the O antigen may be beneficial since immunogenic compositions will elicit both serotype specific and additional cross-reactive immune responses. Absence of hexa-acylated lipid A in the LPS is preferred. Loss of the virulence plasmid leads to loss of the msbB2 gene, and the chromosomal msbB1 gene can be inactivated, thereby removing myristoyl transferase activity and providing a penta-acylated lipid A in the LPS. For *S. flexneri* msbB mutants, absence of the virulence plasmid which contains the msb2 gene, is preferred. Preferred *Shigella* strains for use in the invention have penta-acylated LPS. Alternatively, inactivation of htrB results in loss of the lauroyl chain and thus can yield penta-acylated LPS in some strains and/or forms of lipid A that are less toxic than wild type lipid A. For example, in *S. flexneri*, inactivation of htrB may be compensated for by the activity of another enzyme, LpxP that results in hexa-acylated lipid A, wherein the lauroyl-chain is replaced by a palmitoleoyl chain. Hexy-acylated lipid A comprising palmitoleoyl chains is less toxic than wild type lipid A. Thus, in some embodiments, the invention provides an immunogenic composition comprising GMMA purified from *Shigella sonnei* and *Shigella flexneri* wherein the GMMA comprise penta-acylated lipid A and or hexa-acylated lipid A wherein the lauroyl-chain is replaced by a palmitoleoyl chain. Particularly, suitable strains for use in the invention include the following mutations (a) *Shigella sonnei*: ΔtolR, ΔhtrB, virG::nadAB, (b) *Shigella flexneri* 2a: ΔtolR, ΔmsbB, (c) *Shigella flexneri* 3a: ΔtolR, ΔmsbB and (d) *Shigella flexneri* 6: ΔtolR, ΔmsbB or ΔhtrB. Suitable strains are disclosed in the examples. Other suitable strains are known in the art, for example in WO2011/036564. Culture conditions for growing *Shigella* are well known in the art e.g. see references [12] to [14]. For example, they may be grown using an organic nitrogen source (such as amino acid mixtures e.g. containing Ala, Arg, Asn, Asp; casamino acids may be used), glycerol as a carbon source, etc. Inclusion of L-aspartic acid in the medium is particularly useful and may function as both a nitrogen and carbon source.

For *S. sonnei*, the O-antigen genes are on the virulence plasmid and an OAg component is desirable for GMMA purified or isolated therefrom. Thus, in some embodiments the *S. sonnei* strain is mutated to replace virG with nadA and nadB from *E. coli* thereby removing the nicotinic acid auxotrophy of *Shigella* whilst retaining the virulence plasmid; production of the plasmid encoded OAg is ensured by growth in medium without nicotinic acid. An exemplary mutant *S. sonnei* strain may include the following modifications: ΔtolR::kan ΔvirG::nadAB ΔhtrB::cat.

Exemplary mutant *S. flexneri* strains may include the following modifications: ΔtolR::kan ΔhtrB::cat or ΔtolR::kan ΔmsbB1::cat. Only the msbB1 mutation is introduced into the plasmid-cured strain because removal of the plasmid removes the second copy of msbB (msbB2).

Generalised Modules for Membrane Antigens (GMMA)

*Shigella* bacteria used in the invention are, relative to their corresponding wild-type strains, hyperblebbing i.e. they release into their culture medium larger quantities of GMMA than the wild-type strain. These GMMA are useful as components of *Shigella* vaccines of the invention. The term GMMA is used to provide a clear distinction from conventional detergent-extracted outer membrane vesicles (dOMV), and native outer membrane vesicles (NOMV), which are released spontaneously from Gram-negative bacteria. GMMA differ in two crucial aspects from NOMV. First, to induce GMMA formation, the membrane structure has been modified by the deletion of genes encoding key structural components, specifically tolR. Second, as a consequence of the genetic modification, large quantities of outer membrane "bud off" (the Italian word for bud is 'gemma') to provide a practical source of membrane material for vaccine production, leading to increased ease of manufacturing and potential cost reduction. While NOMV have been used for immunogenicity studies, the yields are too low for practical vaccines.

*S. sonnei* GMMA used in the invention typically have a diameter of from 25 nm to 140 nm by electron microscopy, for example from 25 nm to 40 nm. GMMA may also have a bimodal size distribution. For example, the majority of GMMA having an average size from 25 nm to 40 nm in diameter (by EM) and a fraction of the particles having an average size from 65 nm to 140 nm. Particularly, at least 70%, at least 71%, at least 72%, at least 73%, at least 74%, at least 75%, at least 80%, at least 85%, at least 90% of the GMMA will have a diameter of from 25 nm to 140 nm.

GMMA are released spontaneously during bacterial growth and can be purified from the culture medium. The purification ideally involves separating the GMMA from living and/or intact *Shigella* bacteria, for example, by size-based filtration using a filter, such as a 0.2 µm filter, which allows the GMMA to pass through but which does not allow intact bacteria to pass through, or by using low speed centrifugation to pellet cells while leaving GMMA in suspension. Suitable purification methods are known in the art. A preferred two-step filtration purification process is described in WO2011/036562 herein incorporated by reference. Particularly the two-step filtration process is used to separate GMMA from cell culture biomass without using centrifugation.

GMMA containing compositions of the invention will generally be substantially free from whole bacteria, whether living or dead. The size of the GMMA means that they can readily be separated from whole bacteria by filtration e.g. as typically used for filter sterilisation. Although GMMA will pass through a standard 0.22 µm filters, these can rapidly become clogged by other material, and so it may be useful to perform sequential steps of filter sterilisation through a series of filters of decreasing pore size before using a 0.22 µm filter. Examples of preceding filters would be those with pore size of 0.8 m, 0.45 µm, etc. GMMA are spontaneously-released from bacteria and separation from the culture medium, for example, using filtration, is convenient. Outer membrane vesicles formed by methods which involve deliberate disruption of the outer membrane (e.g. by detergent treatment, such as deoxycholate-extraction, or sonication) to cause outer membrane vesicles to form are excluded from the scope of the invention. GMMA used in the invention are substantially free from inner membrane and cytoplasmic contamination and contain lipids and proteins.

Immunogenic Compositions

Immunogenic compositions of the invention may comprise GMMA purified from at least two, three, four, five or six different strains of *Shigella*. Particularly immunogenic compositions comprise GMMA purified from *Shigella sonnei* and *Shigella flexneri*. The *Shigella flexneri* GMMA may be purified from at least one strain selected from the group consisting of 2a, 3a and 6. Particularly, the immunogenic composition comprises *Shigella flexneri* GMMA purified from each of strains 2a, 3a and 6. The immunogenic composition may further comprise *Shigella flexneri* GMMA purified from at least one strain selected from the group consisting of 1b and 2b. In one embodiment, the immunogenic composition comprises GMMA purified from (a) *Shigella sonnei*, (b) *Shigella flexneri* 2a, (c) *Shigella flexneri* 3a and (d) *Shigella flexneri* 6. In certain embodiments, the immunogenic composition comprises GMMA purified from *Shigella sonnei* 53G, *Shigella flexneri* 2a 2457T, *Shigella flexneri* 3a 6885 and *Shigella flexneri* 6 10.8537 and optionally *Shigella flexneri* 1b STANSFIELD and/or *Shigella flexneri* 2b 69/50.

Where at least two different types of GMMA are used, they may be present in a ratio of 1:1, 1:2, 1:3, 1:4, 2:1, 3:1 or 4:1, preferably about 1:1. Particularly, at least two of the four different GMMA in the immunogenic composition are present at a ratio of from 1:4 to 4:1 Where GMMA from at least four different serotypes are used, they may be present in a ratio selected from the options provided in the table below, for example, a ratio of 1:1:1:1 (ratio option 1). When referring to such ratios, it will be apparent that it will generally be difficult to formulate an immunogenic composition having the exact ratio and that some variability will exist.

| S. sonnei (Ss), S. flexneri 2a (2a), S. flexneri 3a (3a) & S. flexneri 6 (6) | | | | | |
|---|---|---|---|---|---|
| Ratio option | Ss:2a:3a:6 | Ratio option | Ss:2a:3a:6 | Ratio option | Ss:2a:3a:6 |
| 1 | 1:1:1:1 | 23 | 1:4:2:2 | 45 | 2:4:2:1 |
| 2 | 1:1:1:2 | 24 | 1:4:2:4 | 46 | 2:4:4:1 |
| 3 | 1:1:1:4 | 25 | 1:4:4:1 | 47 | 4:1:1:1 |
| 4 | 1:1:2:1 | 26 | 1:4:4:2 | 48 | 4:1:1:2 |
| 5 | 1:1:2:2 | 27 | 1:4:4:4 | 49 | 4:1:1:4 |
| 6 | 1:1:2:4 | 28 | 2:1:1:1 | 50 | 4:1:2:1 |
| 7 | 1:1:4:1 | 29 | 2:1:1:2 | 51 | 4:1:2:2 |
| 8 | 1:1:4:2 | 30 | 2:1:1:4 | 52 | 4:1:2:4 |
| 9 | 1:1:4:4 | 31 | 2:1:2:1 | 53 | 4:1:4:1 |
| 10 | 1:2:1:1 | 32 | 2:1:2:2 | 54 | 4:1:4:2 |
| 11 | 1:2:1:2 | 33 | 2:1:2:4 | 55 | 4:1:4:4 |
| 12 | 1:2:1:4 | 34 | 2:1:4:1 | 56 | 4:2:1:1 |
| 13 | 1:2:2:1 | 35 | 2:1:4:2 | 57 | 4:2:1:2 |
| 14 | 1:2:2:2 | 36 | 2:1:4:4 | 58 | 4:2:1:4 |
| 15 | 1:2:2:4 | 37 | 2:2:1:1 | 59 | 4:2:2:1 |
| 16 | 1:2:4:1 | 38 | 2:2:1:2 | 60 | 4:2:4:1 |
| 17 | 1:2:4:2 | 39 | 2:2:1:4 | 61 | 4:4:1:1 |
| 18 | 1:2:4:4 | 40 | 2:2:2:1 | 62 | 4:4:1:2 |
| 19 | 1:4:1:1 | 41 | 2:2:4:1 | 63 | 4:4:1:4 |
| 20 | 1:4:1:2 | 42 | 2:4:1:1 | 64 | 4:4:2:1 |
| 21 | 1:4:1:4 | 43 | 2:4:1:2 | 65 | 4:4:4:1 |
| 22 | 1:4:2:1 | 44 | 2:4:1:4 | | |

The immunogenic compositions may comprise any suitable amount of GMMA per unit dose. The term "unit dose" refers to an amount of pharmaceutical active, for example an amount of GMMA protein, suitable for administration in one single dose, according to sound medical practice. Suitable amounts of the GMMA protein may be from 0.1 to 200 µg per unit dose, particularly 10 µg, 20 µg, 25 µg, 50 µg or 100 µg. Per unit dose, aqueous immunogenic compositions of the invention may comprise a total concentration of GMMA protein of less than 200 µg/ml, less than 100 µg/ml or less, 80 µg/ml or less, 50 µg/ml or less, 25 µg/ml or less, 20 µg/ml or less, 15 µg/ml or less, 10 µg/ml or less. Per unit dose, aqueous immunogenic compositions of the invention may comprise a total concentration of GMMA protein of from 5 µg/ml to 200 µg/ml, from 5 µg/ml to 100 µg/ml, from 10 µg/ml to 100 µg/ml, from 10 µg/ml to 80 µg/ml, from 10 µg/ml to 50 µg/ml, 25 µg/ml to 50 µg/ml. Per unit dose, immunogenic compositions of the invention may comprise a total concentration of GMMA protein of more than 100 µg/ml, more than 80 µg/ml, more than 50 µg/ml, more than 25 µg/ml, more than 20 µg/ml, more than 15 µg/ml or more than 10 µg/ml. The amount of GMMA can also be quantified by measuring OAg polysaccharide. For example, the OAg polysaccharide to protein ratio (OAg:protein, expressed in terms of w/w) may be in the range of, from 0.06 to 1.1 µg OAg/µg protein, from 0.65 to 1.1 µg OAg/µg protein, 0.75 to 1.1 µg OAg/µg protein or from 0.85 to 1.0 µg OAg/µg protein. Particularly, for S flexneri 2a the OAg:protein ratio may be from 0.85 to 1.0 µg OAg/µg protein, for S. flexneri 3a the OAg:protein ratio may be from 0.75 to 1.1 µg OAg/µg protein, for S. sonnei and S. flexneri 6, the OAg:protein ratio may be from 0.06 to 1.0 µg OAg/µg protein, particularly about 0.06 µg OAg/µg protein. Thus, based on an OAg:protein ratio of 0.75 µg OAg/µg protein, particular amounts of GMMA per unit dose may as above in the range of from 150-200 µg/ml and based on an OAg:protein ratio of from 0.8 to 1.0 µg OAg/µg protein, particular amounts of GMMA per unit dose may be as above particularly in the range from 160-200 µg/ml.

GMMA protein from each different serotype may be present at an amount from 0.1 to 200 µg, for example from 0.1 to 80 µg, 0.1 to 100 µg and in particular from 5 to 25 µg. Suitable amounts of GMMA from each different serotype may include 0.1, 1, 5, 10, 20, 25, 30, 35, 40, 45, 50, 60, 70, 80, 90 and 100 µg per unit dose Immunogenic compositions of the invention include GMMA purified or isolated from more than one strain of Shigella and it is typical for the GMMA to be prepared separately prior to mixing with pharmaceutically acceptable excipients, such as buffers. The GMMA from each strain may be individually formulated with an adjuvant, such as ALHYDROGEL®, prior to combining with GMMA purified or isolated from another strain and mixing with pharmaceutically acceptable excipient(s). Alternatively, the GMMA from each strain may be purified/isolated, combined with GMMA purified or isolated from the other strain(s), formulated with an adjuvant and then mixed with pharmaceutically acceptable excipient(s). Other methods will be apparent to one skilled in the art.

The terms "purified" and "isolated" are generally taken to have the meaning of the art. Preferably purified or isolated GMMA are cell-free preparations, yet more preferably the GMMA have low levels of cytoplasmic protein contamination, for example, less than 10%, less than 9%, less than 8%, less than 7%, less than 6%, less than 5% or less than 4%. For example, measured using high-sensitivity mass spectrometry with label-free Intensity-Based Absolute Quantification Index (iBAQ) compared to compositions of solubilized cells of the GMMA-producing strains, particularly nearly all of the protein content in the GMMA is derived from outer membrane or periplasmic localized proteins, particularly greater than 90%, yet more particularly greater than 95%, greater than 96%, greater than 97%, greater than 98% or greater than 99%. Thus, greater than 95% of the protein content in the GMMA comprises periplasmic or outer membrane localized proteins. Particularly, purified/isolated GMMA comprise an approximately 10-fold enrichment of both periplasmic and outer membrane proteins in GMMA compared to total cell proteins of the GMMA-producing strains.

Briefly, the immunogenic compositions of the invention may be administered in single or multiple doses. A single dose of the immunogenic compositions of the invention may be effective. Alternatively, one unit dose followed by a second unit dose may be effective. Typically, the second (or third, fourth, fifth etc.) unit dose is identical to the first unit dose. The second unit dose may be administered at any suitable time after the first unit dose, in particular after 1, 2 or 3 months. Typically, the immunogenic compositions of the invention will be administered intramuscularly, e.g. by intramuscular administration to the thigh or the upper arm as described below but may also be administered intradermally or intranasally.

Immunogenic compositions of the invention may include one or more adjuvants. Particular adjuvants include aluminium adjuvants, for example, aluminium hydroxide, ALHYDROGEL®, aluminium phosphate, potassium aluminium sulphate and alum. The use of aluminium adjuvants is advantageous since adsorbtion of GMMA to the adjuvant reduces the pyrogenic response allowing, in rabbits, 100 times higher doses of GMMA to be administered compared to GMMA alone. The use of other adjuvants that also reduce the pyrogenic response is also envisaged and could be identified by the skilled person using the tests exemplified below. Whilst the term "adjuvant" generally refers to any substance that increases the immune response to an antigen, in the present case, and without wishing to be bound by hypotheses, the adjuvant, such as ALHYDROGEL®, is also an adsorbant reducing the immune response to the GMMA. Thus, the term "adsorbant" refers to a solid substrate or material to which the GMMA may bind, attach or adsorb (for example, by Van der Waals interactions or hydrogen bonding) such that the pyrogenic response to GMMA is reduced in comparison to GMMA that are not so bound, attached or adsorbed. By way of non-limiting example, immunogenicity of GMMA may be measured by comparing anti-LPS antibody response.

Pharmaceutical Methods and Uses

The immunogenic compositions of the invention may further comprise a pharmaceutically acceptable carrier. Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art Immunogenic compositions of the invention may also contain diluents, such as water, saline, glycerol, etc. Additionally, auxiliary substances, such as wetting or emulsifying agents, pH buffering substances, and the like, may be present. Sterile pyrogen-free, Tris-buffered physiologic saline is a preferred carrier particularly when using aluminium adjuvants since the phosphate in phosphate buffered saline may interfere with GMMA binding to aluminium.

Compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a mammal Such kits may comprise one or more antigens in liquid form and one or more lyophilised antigens. Compositions may be presented in vials, or they may be presented in ready-filled syringes. The syringes may be supplied with or without needles. A syringe will include a single dose of the composition, whereas a vial may include a single dose or multiple doses.

Aqueous compositions of the invention are also suitable for reconstituting other vaccines from a lyophilised form. Where a composition of the invention is to be used for such extemporaneous reconstitution, the invention provides a kit, which may comprise two vials, or may comprise one ready-filled syringe and one vial, with the contents of the syringe being used to reactivate the contents of the vial prior to injection.

Compositions of the invention may be packaged in unit dose form or in multiple dose form. For multiple dose forms, vials are preferred to pre-filled syringes. Effective dosage volumes can be routinely established, but a typical human dose of the composition has a volume of 0.5 ml e.g. for intramuscular injection.

The pH of the composition is preferably between 6 and 8, preferably about 7. For compositions comprising acetylated O-antigens particularly the pH of the composition is less than 7, preferably about 6 (to slow the rate of de-esterification). Stable pH may be maintained by the use of a buffer. The immunogenic compositions of the invention may comprise a Tris [Tris(hydroxymethyl)aminomethane] buffer. The Tris buffer may comprise about 1-20 mM [Tris(hydroxymethyl)aminomethane], e.g. 1.25 mM, 2.5 mM, 5.0 mM or 10.0 mM. For compositions comprising acetylated O-antigens particularly the buffer is not a Tris buffer. The immunogenic compositions of the invention may comprise a 5-20 mM succinate buffer, e.g. 5 mM, 7.5 mM, 10 mM, 12.5 mM, 15 mM, 17.5 mM or 20 mM. The immunogenic compositions of the invention may comprise a 5-20 mM histidine buffer, e.g. 5 mM, 7.5 mM, 10 mM, 12.5 mM, 15 mM, 17.5 mM or 20 mM. The composition will be sterile. Compositions of the invention may be isotonic with respect to humans.

Thus, compositions of the invention may be useful as vaccines. Vaccines according to the invention may either be prophylactic (i.e. to prevent infection) or therapeutic (i.e. to treat infection), but will typically be prophylactic. The term "protected against infection" means that the immune system of a subject has been primed (e.g. by vaccination) to trigger an immune response and repel the infection. It will be clear to those skilled in the art that a vaccinated subject may thus get infected, but is better able to repel the infection than a control subject. The term "treating" includes both therapeutic treatment and prophylactic or preventative treatment, wherein the object is to prevent or lessen infection. For example, treating may include directly affecting or curing, suppressing, inhibiting, preventing, reducing the severity of, delaying the onset of, reducing symptoms associated with, for example, infection, or a combination thereof. "Preventing" may refer, inter alia, to delaying the onset of symptoms, preventing relapse of a disease, and the like. Treating may also include "suppressing" or "inhibiting" an infection or illness, for example reducing severity, number, incidence or latency of symptoms, ameliorating symptoms, reducing secondary symptoms, reducing secondary infections, prolonging patient survival, or combinations thereof. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Compositions of the invention may include an antimicrobial, particularly when packaged in multiple dose formats. Compositions of the invention may include sodium salts (e.g. sodium chloride) to give tonicity. A concentration of 10±2 mg/ml NaCl is typical. In some embodiments, a concentration of 4 to 10 mg/ml NaCl may be used, e.g. 9.0, 7.0, 6.75 or 4.5 mg/ml. Compositions of the invention will generally include a buffer.

Methods of Treatment

The invention also provides a method for raising an immune response in a mammal, comprising administering a pharmaceutical composition of the invention to the mammal. The immune response is preferably protective and preferably involves antibodies. The method may raise a booster response.

The mammal is preferably a human. Where the vaccine is for prophylactic use, the human may be an adult, a child (e.g. a toddler or infant) or a teenager; where the vaccine is for therapeutic use, the human is preferably child. A vaccine intended for children may also be administered to adults e.g. to assess safety, dosage, immunogenicity, etc. A preferred class of humans for treatment are females of child-bearing age (e.g. teenagers and above). Another preferred class is pregnant females.

The invention also provides a composition of the invention for use as a medicament. The medicament is preferably able to raise an immune response in a mammal (i e it is an immunogenic composition) and is more preferably a vaccine.

The invention also provides the use of a composition of the invention in the manufacture of a medicament for raising an immune response in a mammal.

These uses and methods are preferably for the prevention and/or treatment of illness caused by *Shigella* e.g. shigellosis, dysentery and associated symptoms including diarrhoea, fever, abdominal pain, tenesmus, etc. These uses and methods are preferably for the prevention and/or treatment of illness caused by both *Shigella sonnei* and *Shigella flexneri*.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml. For human administration, the dose may be about 100 µg measured by protein, for example, delivered in a 0.5 ml dose at a concentration of 200 µg protein/ml. The invention may be used to elicit systemic and/or mucosal immunity. Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

Unless specifically stated, a process comprising a step of mixing two or more components does not require any specific order of mixing. Thus components can be mixed in any order. Where there are three components then two components can be combined with each other, and then the combination may be combined with the third component, etc.

Unless otherwise stated, identity between polypeptide sequences is preferably determined by the Smith-Waterman homology search algorithm as implemented in the MPSRCH program (Oxford Molecular), using an affine gap search with parameters gap open penalty=12 and gap extension penalty=1.

The practice of the present invention will employ, unless otherwise indicated, conventional methods of chemistry, biochemistry, molecular biology, immunology and pharmacology, within the skill of the art. Such techniques are explained fully in the literature.

In some implementations, the term "comprising" refers to the inclusion of the indicated active agent, such as recited polypeptides or GMMA, as well as inclusion of other active agents, and pharmaceutically acceptable carriers, excipients, emollients, stabilizers, etc., as are known in the pharmaceutical industry. In some implementations, the term "consisting essentially of" refers to a composition, whose only active ingredient is the indicated active ingredient(s), however, other compounds may be included which are for stabilizing, preserving, etc. the formulation, but are not involved directly in the therapeutic effect of the indicated active ingredient. Use of the transitional phrase "consisting essentially" means that the scope of a claim is to be interpreted to encompass the specified materials or steps recited in the claim, and those that do not materially affect the basic and novel characteristic(s) of the claimed invention. See, In re Herz, 537 F.2d 549, 551-52, 190 USPQ 461, 463 (CCPA 1976) (emphasis in the original); see also MPEP § 2111.03. Thus, the term "consisting essentially of" when used in a claim of this invention is not intended to be interpreted to be equivalent to "comprising". The term "consisting of" and variations thereof includes including and limited to unless expressly specified otherwise. The term "about" in relation to a numerical value x means, for example, x+10%, x+5%, x+4%, x+3%, x+2%, x+1%,

MODES FOR CARRYING OUT THE INVENTION

*S sonnei* Strain Generation

*S. sonnei* 53G [15] was chosen as parent strain. *S. sonnei* strain NVGH1859 (*S. sonnei* 53G ΔtolR::kan ΔvirG::nadAB) was obtained by replacing the plasmid-encoded virG gene [16] in *S. sonnei* 53G ΔtolR::kan [17] with the genes nadA and nadB from *E. coli* [18]. The upstream and downstream regions of virG were amplified using the primer pairs virGup-5/virGup-3 (upstream) and virGdown-5/virGdown-3 (downstream) (Table 1). The "nadAB" cassette was generated by amplifying nadA and nadB from *E. coli* using primers nadA-5/nadA-3 and nadB-5/nadB-3 (Table 1). The fragments were inserted into pBluescript (Stratagene) so that nadA and nadB were linked and interposed the flanking regions of virG. The replacement construct (virGup-nadAB-virGdown) was amplified using the primers virGup-5/virGdown-3 and used to transform recombination prone *S. sonnei* ΔtolR::kan as previously described [17].

*S. sonnei* strain NVGH1790 (*S. sonnei* 53G ΔtolR::kan ΔvirG::nadAB ΔhtrB::cat) was generated from NVGH1859 by replacing the htrB gene [19] by the chloramphenicol resistance gene cat as described by Rossi et al. [20].

TABLE 1

Primers used in this study for generation of S. sonnei GMMA producing strains

| Primer | SEQ ID No: | Sequence 5' → 3' |
|---|---|---|
| virGup-5 | 1 | ACTCGAGCTCTGTAGTTGATTTGACAGTTGACATCC |
| virGup-3 | 2 | CTAACCCGGGCACTATATTATCAGTAAGTGGTTGATAAACC |
| virGdown-5 | 3 | CTAACCCGGGCGTGTTGATGTCCTGC |
| virGdown-3 | 4 | ACGCGTCGACAGTTCAGTTCAGGCTGTACGC |
| nadA-5* | 5 | CTAACCCGGGCAAGCAACTCTATGTCGGTGGAAT |
| nadA-3* | 6 | TATCAAGCTTGGCAAGGCCAATACACAGC |
| nadB-5* | 7 | TATCAAGCTTAGGGTTAGAGTGTCTCGTTTTTGTA |
| nadB-3* | 8 | CTAACCCGGGCCAGACCAGAACTATTCC |

*nadA and nadB primers as described by Prunier et al. [18] with small modifications S. flexneri 2a Strain Generation S. flexneri mutants were prepared as previously described in J Biol Chem. 2014 Sep. 5; 289(36): 24922-24935. S. flexneri 2a 2457T was chosen as parent strain. For generation of mutants from S. flexneri 2a without virulence plasmid, a white colony was selected by white appearance on Congo red agar before the start of the genetic modification. The curing of the virulence plasmid (pINV) was confirmed by the absence of the origin of replication (ori) and the plasmid-encoded genes, virG and ospD3, using PCR. The primers are listed in Table 2. To generate the tolR deletion in S. flexneri 2a and plasmid-cured S. flexneri 2a-pINV, the same strategy and primers as described previously for the generation of the S. sonnei ΔtolR mutant (2) were used.

The null mutation of msbB1, or htrB, was obtained by replacing the gene of interest with an antibiotic resistance cassette, using the following strategy. The upstream and downstream regions were amplified using the primer pairs gene-U and gene-D. The resistance cassette used to replace the gene was amplified using primer pairs EcoRV.Ery.F/EcoRV.Ery.R or EcoRV.Cm.F/EcoRV.Cm.R. The fragments were inserted into pBluescript (Stratagene) so that the antibiotic resistance gene interposed the flanking regions of gene. The replacement construct (upstream region-resistance cassette-downstream region) was amplified using the primers binding to the 5' end of the upstream flanking region and the 3' end of the downstream flanking region of gene (see Table 2) and used to transform S. flexneri. In S. flexneri 2a, msbB1 and htrB were replaced by cat. Only the msbB1 mutation needed to be introduced into the plasmid-cured strain as the plasmid carries the second copy of msbB (msbB2) and this is absent in a plasmid cured strain. For simplicity, the mutant is referred to as ΔmsbB. S. flexneri 2a strain NVGH2404 (S. flexneri 2457T ΔtolR::kan, ΔmsbB::cat) was generated.

TABLE 2

Primers used in this study for generation of S. flexneri 2a GMMA producing strains

| Primer name | SEQ ID NO: | Sequence 5' → 3' |
|---|---|---|
| htrB-U1 Xba Sma | 9 | CTAGTCTAGAAACCCGGGCAATTGTATGTATTGTCG |
| htrB-soU2 SacI | 10 | ACTCGAGCTCCCGTCATCATCCAACGC |
| htrB-flexU2 SacI | 11 | ACTCGAGCTCATCCGATATACGTTCGCCC |
| htrB-soD1 SalI | 12 | ACGCGTCGACCTCAGTAATCAGGGTTCTTTG |
| htrB-soD2 SmaI | 13 | CTAACCCGGGTAAATCTCCCCTGCCGGATG |
| htrB-flexD1 SalI | 14 | ACGCGTCGACCCTGTAATCTCAGGTCAAATG |
| htrB-flexD2 SmaI | 15 | CTAACCCGGGTAAATCTCCCATGCCGGATG |
| msbB-flexU5 Sma | 16 | CTAGTCTAGAAACCCGGGTGATAGTGTAGCGGCACA |
| msbB-flexU3 Sac | 17 | ACTCGAGCTCGTGAGCAAAGCCAGCTG |
| msbB-flexD5 SalI | 18 | ACGCGTCGACCTCGGTGTGGAAATTGG |
| msbB-flexD3 Xba Sma | 19 | CTAACCCGGGCAACGTACTTACTCTACCG |
| P1.htrBcompl-EcoRI | 20 | ACCGGAATTCGTGTAACACTGGCATGGTGTA |
| P2.htrBcompl-NcoI | 21 | CATGCCATTGTAGCAATCCGCTGTTGGTGCG |
| EcoRV.Ery.F | 22 | AGCTTGATATCAGAGTGTGTTGATAGTGCAGTATC |
| EcoRV.Ery.R | 23 | AGCTTGATATCACCTCTTTTAGCTTCTTGGAAGCT |
| EcoRV.Cm.F | 24 | AGCTTGATATCTGTGACGGAAGATCACTTCG |
| EcoRV.Cm.R | 25 | AGCTTGATATCGGGCACCAATAACTGCCTTA |
| Ori-1 | 26 | CGGCATCAGAATAATACAAGCAGC |
| Ori-2 | 27 | AGGTGTACCGTGCTCTGGG |

TABLE 2-continued

Primers used in this study for generation of S. flexneri 2a GMMA producing strains

| Primer name | SEQ ID NO: | Sequence 5' → 3' |
|---|---|---|
| virG-1 | 28 | GTCACAGGTAACATGACTCTGGAG |
| virG-2 | 29 | CCATGTGTGAATACTACCTTCACCC |
| ospD3-1 | 30 | GTTTTGCCTCATTCAAGATATCACC |
| ospD3-2 | 31 | TGACGATGGTTTGTCAGGATTGC |
| msbB.F | 32 | CGCCAAAGTTCCGTGATCCCATT |
| msbB.R | 33 | CTCTTCGATGATCTCCAGCCCTT |

S. flexneri* 1b, 2b, 3a and 6 generation

*S. flexneri* 1b, 2b, 3a and 6 mutants were prepared by adapting the methods described in [32].

Strains

*Shigella flexneri* 1b STANSFIELD, *Shigella flexneri* 2b 69/50, *Shigella flexneri* 3a 6885 and *Shigella flexneri* 6 10.8537 were chosen as parent strains. For generation of mutants without virulence plasmid, a white colony was selected by white appearance on Congo red agar before the start of the genetic modification. The curing of the virulence plasmid (pINV) was confirmed by the absence of plasmid-encoded virulence genes, particularly virG (primers 88/89) and mxiA (primers 53/54), using PCR. The primers are listed in Table 3.

To generate the tolR deletion in *S. flexneri* 1b, 2b, 3a, and 6, the kanamycin cassette was amplified from plasmid pKD4 [32] using primers 45/46 (Table 3). The replacement of the tolR gene in strains carrying the plasmids pKD46 or pAJD434 was confirmed by PCR (primers 39/40). Removal of the antibiotic selective marker was performed as described in [32], using the plasmid pCP20. The same strategy was used for the deletion of htrB and msbB genes in these strains, using primers 49/50 and 51/52, respectively, for the amplification of the chloramphenicol cassette obtained by PCR from plasmid pKD3 (primers 45/46). Alternatively, the replacement of htrB and msbB was performed using the fragment obtained from the amplification of the chloramphenicol cassette by the primers 78-81 and 74-77 (Table 3), respectively. Replacement of htrB and msbB genes was verified by PCR using primers 82/83 and 55/56, respectively. The chloramphenicol selective marker (cat) was removed as described [32]. *S. flexneri* 3a strain NVGH2766 (*S. flexneri* 6885 ΔtolR::kan, ΔmsbB::cat) was generated.

TABLE 3

Primers used in the generation of *S. flexneri* 1b, 2b, 3a and 6 mutants

| Primer name | SEQ ID No: | Sequence 5'-3' |
|---|---|---|
| 45-pKDF | 34 | CACGTCTTGAGCGATTGTGTAGG |
| 46-pKDR | 35 | GACATGGGAATTAGCCATGGTCC |
| 39-tolRsF | 36 | CAATTGGTCTGTTCGCCGC |
| 40-tolRsR | 37 | CTACCGCACCTGAATCAACCA |
| 47-tolRKOF | 38 | ACCGCCAGGCGTTTACCGTTAGCGAGAGCAACAAGGGGTAAGCCATGGCCG TGTAGGCTGGAGCTGCTTC |
| 48-tolRKOR | 39 | ACCCGCTCTCTTTCAAGCAAGGGAAACGCAGATGTTTAGATAGGCTGCGTCA TATGAATATCCTCCTTAG |
| 49-htrBKOF | 40 | ACAATACATACAATTGCCCGTATAGGTTGAAAAACAGGATTGATATGACGGT GTAGGCTGGAGCTGCTTC |
| 50-htrBKOR | 41 | ATGCCGGATGCCATTCTGAAGCATCCGGCATGGGAGATTTAATAGCGTGACA TATGAATATCCTCCTTAG |
| 51-msbBKOF | 42 | ACTATCACCAGATTGATTTTTGCCTTATCCGAAACTGGAAAAGCATGGAAGT GTAGGCTGGAGCTGCTTC |
| 52-msbBKOR | 43 | TTTTATTTGATGGGATAAAGATCTTTGCGCTTATACGGCTGGATTTCGCCCAT ATGAATATCCTCCTTAG |
| 53-mxiAF | 44 | CGATAGGGATGTTGCCAGGTT |

TABLE 3-continued

Primers used in the generation of S. flexneri 1b, 2b, 3a and 6 mutants

| Primer name | SEQ ID No: | Sequence 5'-3' |
|---|---|---|
| 54-mxiAR | 45 | CTATCGGCACGCACCTCATTTA |
| 55-msbB2F | 46 | CTTTCCCCTGTTTACTGGTTTACA |
| 56-msbB2R | 47 | TGTCCGCGCTGGCAATG |
| 74-msbBKOuF | 48 | AACCCGCGTCGAACTAATCC |
| 75-msbBKOuR | 49 | CCTACACAATCGCTCAAGACGTGCGTTTCCATGCTTTTCCAGTTT |
| 76-msbBKOdF | 50 | GGACCATGGCTAATTCCCATGTCCCCATCAAATAAAAAAGCCTCTCG |
| 77-msbBKOdR | 51 | ATCCCGAGCATCAACGTTTC |
| 78-htrBKOuF | 52 | GCGCAGTACCCAGAAGGAT |
| 79-htrBKOuR | 53 | CCTACACAATCGCTCAAGACGTGGGTGGAGAACTTGGGTAGATTCG |
| 80-htrBKOdF | 54 | GGACCATGGCTAATTCCCATGTCCCTTCACGCTATTAAATCTCCCA |
| 81-htrBKOdR | 55 | TGACTACATCTACACCAGCCCT |
| 82-htrBF | 56 | GCGTACTTTGGTTGGTCGTG |
| 83-htrBR | 57 | AACGAAGGGCACCAGACA |
| 88-virGF | 58 | GGTTATGATGGCTACGGTGGTA |
| 89-virGR | 59 | GTTTATAGTCCTTCTGCGCCCA |
| 74-msbBKOuF | 60 | AACCCGCGTCGAACTAATCC |
| 75-msbBKOuR | 61 | CCTACACAATCGCTCAAGACGTGCGTTTCCATGCTTTTCCAGTTT |
| 76-msbBKOdF | 62 | GGACCATGGCTAATTCCCATGTCCCCATCAAATAAAAAAGCCTCTCG |
| 77-msbBKOdR | 63 | ATCCCGAGCATCAACGTTTC |
| 78-htrBKOuF | 64 | GCGCAGTACCCAGAAGGAT |
| 79-htrBKOuR | 65 | CCTACACAATCGCTCAAGACGTGGGTGGAGAACTTGGGTAGATTCG |
| 80-htrBKOdF | 66 | GGACCATGGCTAATTCCCATGTCCCTTCACGCTATTAAATCTCCCA |
| 81-htrBKOdR | 67 | TGACTACATCTACACCAGCCCT |

*Shigella* Growth Conditions

*Shigella sonnei* and *Shigella flexneri* GMMA production strains were routinely cultured in *S. sonnei* Defined Medium (SSDM, [17]) with glucose as carbon source. The SSDM was prepared as follows: 13.3 g/kg KH2PO4, 4 g/kg (NH4)2HPO4, 1.7 g/kg citric acid monohydrate, 2.5 g/kg L-aspartic acid, 493 mg/kg MgSO4*H2O, 2.7 mg/kg Co(NH3)6Cl3, 15 mg/kg MnCl$_2$*4H$_2$O, 1.5 mg/kg CuCl$_2$*H2O, 3 mg/kg H$_3$BO$_3$, 2.5 mg/kg Na$_2$MoO$_4$*2H$_2$O, 2.5 mg/kg zinc acetate monohydrate, 0.49 mg/kg ferric citrate, 50 mg/kg thiamine. Glucose was added at a concentration of 5 g/kg for solid medium and shake flask cultures. For growth in fermenters, 27.3 g/kg glucose and 0.25 g/kg polypropylene glycol (PPG) were added. Solid SSDM contained 18 g/L agar. *Shigella flexneri* media was further supplemented with amino acids, vitamins, and higher concentration of iron.

Cell Banking

To minimize the risk of contamination with transmissible spongiform encephalitis (TSE) or other adventitious agents, the *S. sonnei* cell line was and the *S. flexneri* cell lines are cleaned under GMP by three passages on agar plates prepared with SSDM. GMP master and or working cell bank vials are prepared.

Flow Cytometry of Bacteria or GMMA

*Shigella* bacteria from fermenter or flask scale culture were preserved for flow cytometry analysis by fixation in 0.5% formaldehyde. $9 \times 10^4$ to $9 \times 10^5$ cells were stained with monovalent rabbit antiserum (Denka Seiken Co., Ltd.), reacting with the O antigen (OAg) or polyclonal mouse antiserum raised against ALHYDROGEL®-formulated GMMA for *Shigella* serotypes. Bound antibodies were detected using Fluorescein-conjugated F(ab')2 fragment goat anti-rabbit or anti-mouse IgG, IgM or IgA (Jackson ImmunoResearch Europe Ltd.). Samples were fixed using 4% formaldehyde and analyzed using a FACScanto™ II flow cytometer (BD Biosciences). The data were processed using FlowJo software (Tree Star Inc.).

GMMA Production

The descriptions that follow are based on the production of *S. sonnei* 1790-GMMA. Where the process differs for the production of GMMA from *S. flexneri*, additional indications are given.

Fermentation

For each production batch, the *Shigella* strain was grown in a shake flask from the Research or GMP cell bank in SSDM at 30° C. with agitation (200 rpm), starting from an optical density measured at 600 nm (OD600) of 0.02 until the culture reached an OD600 equal to 1.5±0.5, usually in 9±2 hours. In the Bioreactor (30 L scale in Sartorius, Biostat D75 Bioreactor, or 25 L scale in LP35 Bioengineering Bioreactor), strains are cultured in Batch mode starting from 2% inoculum size with controlled cultivation conditions: pH 6.7 kept by addition of 28% NH4OH, 30° C., dissolved oxygen kept at 30% saturation by 1 air volume per culture volume per minute (vvm) airflow, agitation and pressure in cascade (200-800 rpm, 50-1250 mbarg) until the final OD600 of 35.

Purification

GMMA released into the fermentation broth were purified using two consecutive Tangential Flow Filtration (TFF) steps: a microfiltration in which the culture supernatant containing the GMMA is separated from the bacteria, and an ultrafiltration, in which the GMMA were separated from soluble proteins. For the microfiltration step (1.2 m2 of a 0.2 μm pore size cellulose membrane) the bioreactor was connected with the TFF system, in order to use the fermentation vessel as a recirculation tank. The culture supernatant was initially concentrated three times to reach "one volume" of concentrated supernatant, followed by a discontinuous diafiltration against five volumes of the buffer in the growth medium (13.3 g/kg of KH2PO4; 4 g/kg of NH4HPO4; 1.7 g/kg of Citric acid; 4 mL/L of NH4OH; pH 6.7). Physiological saline can also be used. The microfiltered material, containing GMMA, was then filtered through a filter capsule with 0.45 μm then 0.2 μm filters (Sartorius) to ensure absence of any viable *Shigella* bacteria before further processing. The ultrafiltration step (1.4 m2 of a 300 kDa pore size PES membrane) consisted of concentration followed by continuous diafiltration of the microfiltered GMMA solution against ten volumes of Tris-buffered saline (TBS), 0.9% NaCl, 10 mM Tris/Tris HCl pH 7.4 or 0.9% w/v of sodium chloride, and permitted substantial removal of nucleic acids and soluble proteins. A final concentration of the purified GMMA was performed to obtain the required concentration for the formulation process and filtered through a Sartorius cellulose acetate sterilizing filter which was validated for extractables, leachables and bacteria retention capability with GMMA bulk. Three non-GMP consistency batches of *S. sonnei* GMMA were prepared from a fermentation volume of 30 L. Additionally, two GMP lots were produced and released to support the further manufacturing of toxicology and clinical vaccines. The bulk *S. sonnei* GMMA were tested for appearance, identity, total and soluble protein content, 0 antigen content, LPS content, pH osmolality, purity and size.

Formulation

GMMA were adsorbed to aluminium hydroxide (ALHYDROGEL® 2%, Brenntag Biosector, Denmark) by adding the GMMA suspension to ALHYDROGEL® under constant stirring at room temperature for 2 h followed by vialing. The GMMA ALHYDROGEL® formulation contains 12.7 μg/mL *S. sonnei* O antigen, 200 μg/mL GMMA protein and 0.7 mg/mL aluminium-III-ion (A13+) as ALHYDROGEL® in TBS. A histidine buffer can also be used. The formulation was dispensed at 0.7 mL per 3 mL single dose vial. The formulation was tested for identity, total protein content, aluminium content, extractable volume, non-adsorbed protein, visual appearance, pH, osmolality, sterility, immunogenicity, and pyrogenicity.

Three GMP lots of *S. sonnei* 1790GAHB, a toxicology lot and two clinical lots, were prepared and released. A smaller (140 mL) non-GMP stability lot was also generated. Freshly formulated small scale laboratory batches were produced for initial pyrogenicity and immunogenicity studies.

GMP Formulation of GAHB-Placebo

Placebo, also used as diluent, was prepared containing 0.7 mg/mL A13+ as ALHYDROGEL® in TBS and was dispensed at 0.7 mL per 3 mL vial. A histidine buffer can also be used. The GAHB-Placebo was tested for identity, aluminium content, extractable volume, visual appearance, pH, osmolality, sterility and pyrogenicity. Two GMP lots of GAHB-Placebo have been produced and released.

Physico-Chemical Analytical Methods

Protein Quantification of GMMA

GMMA produced from strain NVGH1790 are called 1790-GMMA. Protein quantification was routinely performed by Lowry assay. For determining protein concentration of GMMA, assays used a secondary BSA standard calibrated as previously described [28] against a primary 1790-GMMA standard with a protein content determined by quantitative amino acid analysis. Thus all GMMA protein concentrations are indirectly referenced to the protein concentration determined by amino acid analysis. Samples containing Tris were diluted to a final Tris concentration of equal to or less than 1 mM to avoid interference in the Lowry assay. The microBCA assay can also be used for GMMA protein quantification.

Protein Quantification of ALHYDROGEL® Formulated GMMA

For protein quantification of GMMA adsorbed to ALHYDROGEL® (e.g. 1790GAHB), the Lowry or microBCA assay is also used, and the secondary BSA standard was adsorbed to ALHYDROGEL®. After the colour development, the samples were centrifuged and the absorbances of the supernatants were determined. Soluble protein not adsorbed to GMMA preparations was determined in the supernatant of ALHYDROGEL® formulations following ultracentrifugation at 186,000 g at 4° C. for 2 h using a secondary BSA standard calibrated against a primary soluble protein standard quantified by quantitative amino acid analysis.

The unbound protein content in GMMA adsorbed to ALHYDROGEL® was too low to measure by Lowry or microBCA and was assessed as limit test by SDS-PAGE (10% bis-acrylamide gel) of supernatants collected after centrifugation of the sample and compared with reference 1790-GMMA run in a parallel lane. Protein bands were visualized by silver staining, quantified by densitometry and the data analyzed using ImageScanner III software. The intensity of detectable bands in the supernatant sample was compared (as limit test) to the intensity of the corresponding bands in the 1790-GMMA sample. The limit corresponds to 5 μg/mL of non-adsorbed protein (2.5% of total protein of the 1790GAHB formulation).

GMMA Protein Profile

1790-GMMA were denatured for 10 min at 100° C. in sodium dodecyl sulfate-polyacrylamide gel electrophoresis (SDS-PAGE) sample buffer containing SDS (Invitrogen, LDS NuPAGE sample buffer) and 50 mM dithiothreitol (DTT). 3 μg of protein were loaded onto a 10% (wt/vol) polyacrylamide gel (Invitrogen, Novex 10%). Electrophoresis was carried out in 3-(N-morpholino)-propanesulfonic acid (MOPS) buffer (Invitrogen) at 40 mA for 75 min. The separated proteins were stained with brilliant Blue G-colloidal Coomassie (Sigma-Aldrich), quantified using densitometry and analyzed using ImageScanner III software. Protein profiles of the test samples were compared with profiles of reference GMMA electrophoresed on the same gel.

O Antigen Quantification in GMMA

For detailed characterization and lot release assays, O antigen (OAg) concentration was measured by HPAEC-PAD analysis. The quantification determines the weight in mg of total OAg present in the sample.

O antigen reference standard: GMMA from *S. sonnei* NVGH1859 (1859-GMMA) were hydrolyzed for 2 h 100° C. in 1% acetic acid. The cleaved lipid A and precipitated protein were both removed by centrifugation [21]. The main fraction (medium molecular weight, MMW) of OAg was recovered by Size Exclusion Chromatography (SEC, GE Sephacryl S-100HR column). The OAg size was determined by measuring the number of repeating units by 1H-NMR [22]. The average was 33. The O antigen quantity was determined from the average number of repeating units and the molar concentration of the LPS core by galactose measured by HPAEC-PAD analysis as described above and in LPS quantification below. As an alternative the quantification of OAg can be done by quantitative 1H-NMR (qNMR) using maleic acid as internal standard.

O antigen quantification in GMMA: LPS was purified by hot phenol-water extraction [23] as follows: 400 µL of sample was added to an equal volume of 90% phenol pH 8 solution (Sigma-Aldrich) and incubated at 80° C. for 2 h. After cooling to 4° C., the sample was centrifuged at 18000 g at 4° C. for 15 min and the upper water phase containing the LPS was recovered. The phenol phase was extracted again with 400 µL of water (1 h 80° C.) and after centrifugation (18000 g at 4° C. for 15 min) the water phase recovered, combined with the first water extract and dried overnight in a centrifugal evaporator. The sample was reconstituted in water (400 µL) and eventually diluted with water to give a concentration of O antigen between 2.5 and 30 µg/mL. LPS yield was >90% as judged by the recovery of LPS core, measured using galactose as described above. The LPS was subjected to alkaline hydrolysis and sugars measured by HPAEC-PAD analysis as reported for Vi polysaccharide [40] and compared with the O antigen reference standard.

LPS Quantification in GMMA

Quantitative determination of the core sugar galactose by HPAEC-PAD analysis [21] was used to quantify the amount of LPS in 1790-GMMA based on two galactose per core [22]. The quantification determines the number of moles of LPS molecules. A standard dilution series of galactose is run in each analysis. 1790-GMMA and galactose standard are treated in parallel with 2M trifluoroacetic acid for 4 h at 100° C. Samples are chilled at 2-8° C., dried overnight, re-dissolved in water, filtered and analyzed. HPAEC-PAD is performed on Dionex ICS3000 using CarboPac PA10 column and PA10 guard column. Separation is performed using an isocratic condition eluting with 18 mM NaOH. For *S. flexneri* GMMA, as a general method for quantification of LPS, the quantification of 3-hydroxyfatty acids present as ester in lipid a structure is used. By alkaline hydrolysis of the sample followed by HPLC-RP-QqQ (SRM), quantification is performed using a 3OH-fatty acid standard to build the calibration curve.

LPS Size Distribution in GMMA

For screening purposes SDS-PAGE analysis may be used. LPS was purified using the phenol-water method (see above) with modifications. GMMA (1 mg/mL) were boiled for 3 min, incubated with 0.5 µg/µL proteinase K (Sigma Aldrich) at 60° C. overnight, mixed 1:1 (vol/vol) with saturated phenol pH 8.0 (Sigma Aldrich), incubated for 30 min at 70° C., and centrifuged for 1 h at 10,000 g at room temperature. The upper phase was recovered, mixed 2:1 (vol/vol) with 100% ethanol, LPS was precipitated for 1 h at −80° C. and pelleted by centrifuging at 12,000 g for 30 min at room temperature. The pellet was dried using a SpeedVac and dissolved in water LPS was electrophoresed on 12% bis-tris polyacrylamide gel (Life technologies) and stained using the Silver Quest™ Silver Staining Kit (Life Technologies). For more precise characterization HPLC-SEC may be used. Lipid-A and protein are removed from the test sample by 1% acetic acid hydrolysis (2 h 100° C.)/low speed centrifugation (14000 rcf 5 min); the dried (or desalted) supernatant is injected in HPLC using TSKGEL® 3000 PW column with refractive index detector. The molecular size is determined by GPC software using MW standard dextrans. If the sample is derivatized with semicarbozide, the resulting peak can be used to confirm the quantity of OAg.

MALDI-TOF Analysis of Lipid A in Bacteria or GMMA

The Lipid A identity assay by Matrix-Assisted Laser Desorption/Ionization-time of flight (MALDI_TOF) method determines the type of lipid A in LPS. Lipid A was precipitated from GMMA or bacterial cell banks as previously described [20] using mild acid hydrolysis with 1% acetic acid for 2 h at 100° C. Samples were centrifuged at 14,000 g for 15 min, the pellets resuspended in water, and washed twice with water. The pellets were dried overnight using a Speedvac and resuspended in chloroform-methanol 4:1 and mixed with an equal volume of Super DHB (Sigma-Aldrich) solution in water/acetonitrile 1:1 (vol/vol). Two µL of the mixture were loaded to the target plate (MTP 384 target plate ground steel BC, Bruker Daltonics) and analyzed by Ultraflex MALDI-TOF (Bruker Daltonics) in reflectron ion-negative mode. A Peptide Calibration Standard (Bruker Daltonics), mixed with the Super DHB solution, was included in each analysis. The m/z ratios were determined by Flex Analysis software in comparison to the Peptide Standard. The species of lipid A is identified by comparison of the molecular peak mass m/z to what is expected for the samples.

GMMA Particle Size

Dynamic light scattering determines the size distribution of GMMA using a Malvern Zetasizer Nano ZS™. The particle size distribution was obtained as intensity of the scattered light using the Z-average value of three different measurements of the 173° backscattered light with "protein" as material setting and "General purpose (normal resolution) ". The diameter obtained by this technique is of a sphere that has the same translational diffusion coefficient as the particle being measured. The size is expected to be different to that measured by electron microscopy will be a valid measure of the range of particle sizes and consistency of manufacture.

Negative Staining Transmission Electron Microscopy has also been used to assess the particle size of GMMA. GMMA were prepared and observed by Electron Microscopy as previously described [20]. Electron micrographs were recorded at a nominal magnification of 105,000×. GMMA diameters were measured manually on printed copies of the electron micrographs in comparison to the scale bar. Another technique used for sizing that match better the data obtain by electron microscopy is the HPLC-SEC coupled with MALLS (multi angle laser light scattering) using TSK-GEL® 6000PW and 4000PW column connected in series.

Identity and O Antigen Quantification of ALHYDROGEL® Formulated GMMA

The identity of ALHYDROGEL® formulated GMMA can be determined by immunologic based techniques.

The Direct ALHYDROGEL® Formulation Immunoassay [31] has been employed with modifications. The identity of GMMA is confirmed by detection of the O antigen present in the formulation using a commercial typing antiserum produced in rabbits or typing monoclonal antibody produced in mice. An aliquot of the GMMA-ALHYDROGEL® suspension is blocked with BSA and incubated with the OAg-specific antibody. The binding of the typing antibody is then detected using and enzyme-labelled anti-rabbit antibody or anti-mouse antibody. The presence of immunoreacting O antigen is detected by addition of substrate solution and formation of colour that can be detected by absorbance. Identity is confirmed by comparison of the absorbance of the test sample to the absorbance of a reference included in the same assay.

Identity and O antigen quantification can also be carried out by competitive ELISA. The working principle is based on the competition between *Shigella* specific O antigen or LPS and the ALHYDROGEL® formulated GMMA for binding to a serogroup specific monoclonal antibody or polyclonal antiserum. The more Formulated GMMA that is present in the suspension, the less monoclonal antibody or polyclonal antibody can bind to the antigen coated plate, and the less signal can be detected by standard ELISA methods. The O antigen present in the test formulation is quantified in comparison to the signals obtained with a standard curve built by spiking the monoclonal antibody with a known amount of ALHYDROGEL® formulated GMMA.

Biological Assays
PBMC Isolation and MAT

The in vitro Interleukin 6 (IL-6) production by PBMC following stimulation with GMMA was used as in vitro surrogate to assess reactogenic potential using the procedure described by Rossi et al. [20]. Briefly, buffy coats from different donors were used to isolate PMBC using Ficoll density centrifugation as reported [24]. PBMC were seeded at a density of 2×105 cells/well with 180 µL of RPMI-1640 complemented with 25 mM HEPES, 2 mM glutamine, 10% FBS, 1% Pen-Strep (InvitroGen) in 96-well round bottom plates. 20 µL of 10-fold serial dilutions of GMMA in TBS (0.0001-1,000 ng/mL final concentration in the assay) were added, cells were incubated for 4 h at 37° C. and supernatants were recovered after centrifugation (5 min, 400 g) and stored at −80° C. until analyzed for IL-6 concentration.

Immunogenicity/Potency Studies in Mice

Eight BALB/c mice or CD-1 mice per group (female, 4 to 6 weeks old) received one or two intraperitoneal injections of different doses of GMMA formulated ALHYDROGEL on days 0, and 21 in a volume of 0.5 mL. Control mice received 0.5 mL of GAHB-Placebo. Blood samples were collected on days 7, 14, 21, 28, 35 or in some studies, only on day 21. In potency assays, groups of mice were immunized with four different doses of the vaccine or potency standard (reference GMMA, stored at −80° C., and freshly formulated on ALHYDROGEL).

Enzyme-Linked Immunosorbent Assay (ELISA)

Antibodies elicited to *S. sonnei* or *S. flexneri* GMMA are assessed by ELISA using *Shigella sonnei* LPS or *S. flexneri* serogroup O antigen as plate coating antigen. Nunc™ Maxisorp™ 96-well plates were coated over night at 2-8° C. with 0.5 µg/mL LPS or <5 µg/mL OAg in phosphate-buffered saline (PBS). The plates were blocked for 1 h with 5% milk in PBS and subsequently washed three times with PBS containing 0.05% TWEEN® 20 (PBST). Mouse sera were diluted 1:100 and 1:4000 in PBST with 0.1% BSA, rabbit sera were diluted in 5% milk in PBS. Diluted sera were incubated in triplicate for 2 h in the ELISA pates. The samples were tested in comparison to previously established and calibrated anti-*S. sonnei* LPS or anti-*S. flexneri* serotype O antigen standard sera included in a duplicate series of dilutions on each of the plates. After incubation with sample and reference sera the plates were washed three times as above. Bound antibody was detected using a goat anti-mouse IgG or goat anti-rabbit IgG conjugated to alkaline phosphatase, diluted in PBST, and followed by three washing steps and a colour reaction with p-nitrophenyl phosphate substrate. After 1 h, absorbance (optical density, OD) was measured at 405 nm and 490 nm wavelength and the OD405 nm-490 nm was calculated. Results are expressed in ELISA units determined relative to the standard serum. One ELISA unit equals the reciprocal of the dilution of the standard serum giving an OD405 nm-490 nm of 1 in the standard assay.

Serum Bactericidal Assay as a Measure of Antibody Functionality

*S. sonnei* and *S. flexneri* bacteria were grown to log-phase (OD: 0.2), diluted 1:15,000 in PBS and distributed into sterile polystyrene U bottom 96-well microtiter plates. To each well, serum samples serially diluted 8-12-folds (starting from 1:100 in well dilution) were added. Prior to use sera were heated at 56° C. for 30 min to inactivate endogenous complement. Active Baby Rabbit Complement (BRC, Cederlane CL3441 lot6288) used at 7-20% of the final volume was added to each well. BRC source, lot and percentage used in the SBA reaction mixture were previously selected for low toxicity against each specific bacteria. To evaluate possible nonspecific inhibitory effects of BRC or mouse serum, bacteria were also incubated with the same tested sera plus heat-inactivated BRC; sera alone (no BRC); SBA buffer and active BRC. After 3 h incubation in the SBA mix, bacterial growth inhibition was measured. Bactericidal activity was measured in terms of serum titers, which are defined as serum dilutions necessary to obtain 50% percent bacterial growth. Serum titers equal to 10 were given when no bactericidal activity was detected.

Pyrogenicity

We established a modification of the European Pharmacopeia intravenous pyrogenicity test method (Ph.Eur. 2.6.8 pyrogens, [25]) using the administration of a full human dose delivered intramuscularly. Two sets of experiments were carried out to establish the assay. In the first experiment (under non-GMP conditions but in the GMP facility), three groups of 3 rabbits, preselected according to Ph.Eur. 2.6.8 pyrogens, were placed in retaining boxes and the body temperatures were recorded using a rectal probe and the initial temperature was determined. The toxicology lot of the vaccine (0.5 mL) was injected intramuscularly to each of three rabbits in two vaccine groups and 0.5 mL sterile physiological saline to the three rabbits of the control group. Temperature was recorded continuously by an automated system from 90 min before injection until 3 h after administration to determine the initial temperature and a possible temperature rise after administration. Temperature was recorded manually at 3.5, 4, 5, 5.5, 6, 6.5 and 7 h. The next day, the rabbits were placed back in the retaining box, allowed to acclimatize and another reading taken at 24 h.

On the basis of the data (see Results), the following test was chosen for the intra-muscular pyrogenicity test for 1790GAHB. Two groups of three 3 rabbits, (one vaccine test and one control group), are selected according Ph.Eur. 2.6.8, placed in retaining boxes and the initial temperature determined using a rectal probe. The vaccine (0.5 mL) is injected intramuscularly to rabbits in the vaccine group and 0.5 mL sterile physiological saline to rabbits of the control group. Temperature is recorded continuously by an automated system for 3 h and additional readings are taken manually at 3.5 and 4 h. The maximum temperature rise for each rabbit is determined (the difference between the highest temperature measured during the 4 h period after administration and the initial temperature). For the test to be valid, the mean of the maximum temperature rise of three controls has to be ≤0.3° C. The test passes if the mean maximum temperature rise of three vaccine test rabbits is <0.8° C., and fails if the mean maximum temperature rise is ≥1.2° C. The test will be repeated if the mean maximum temperature rise of the three rabbits is >0.8 but <1.2° C. For the repeat test in 3 additional rabbits, the test would pass if the mean maximum temperature rise of the three rabbits is ≤0.8° C. and otherwise fail. The second study was carried out under GMP conditions in the GMP facility using the criteria above to assess pyrogenicity of the toxicology and the clinical vaccine lots. The temperature recording in the study was extended over a 24 h period to provide further data on the robustness of the assay and the choice of 4 h as the definitive time period to assess temperature rise. The IM pyrogenicity testing method has been used to release three GMP lots of S. sonnei 1790GAHB.

Repeat Dose Toxicology Study

To support the clinical administration of up to three immunizations of S. sonnei 1790GAHB vaccine, a toxicology study was conducted with New Zealand White rabbits in compliance with Good Laboratory Practice (GLP) standards (WIL Research Europe, Lyon, France). Vaccine was administered four times, two-weeks apart by the intramuscular (IM), intranasal (IN), or intradermal (ID) clinical route, followed by a two-week observation period. Rabbits were selected as the animal model based on preliminary research studies demonstrating capability to produce an immune response. The study design is presented in Table 3. All animals were observed during the course of the study for morbidity/mortality, clinical observations/examination, Draize injection sites, ophthalmology, body weights, food consumption. Clinical pathology, including coagulation parameters and C-reactive protein (pretest, on day 2 and at both necropsies), antibody analysis (pretest, predose and at both necropsies), macroscopic observations at necropsies, organs weights, and histopathology (complete WHO tissue list) were also performed in all groups. Body temperatures of groups 2 and 5 (IM) at first immunization were measured at 1.5 h, 0.5 h, and 2 min (0 h) before dosing and at 0.5, 2, 6, and 24 h after injection. The average of the temperature at −0.5 h and 0 h was considered as the initial temperature of the rabbits. At the 2nd, 3rd, and 4th immunizations of groups 2 and 5 and at all immunizations of groups 1, 3, 4, 6, and 7, body temperatures were recorded prior (0 h) and 2, 6, and 24 h after dosing.

TABLE 3

Experimental design of toxicology study

| Group/Treatment | Route(s)[a] | Antigen per injection (μg OAg/ μg protein) | Dose volume per injection (μL) | Number of animals | | | |
|---|---|---|---|---|---|---|---|
| | | | | Necropsied on day 44 | | Necropsied on day 56 | |
| | | | | Males | Females | Males | Females |
| 1[b] 0.9% NaCl | IM | 0 | 500 | 4 | 4 | 4 | 4 |
| | IN[c] | | 400 | | | | |
| | ID | | 50 | | | | |
| 2 GAHB-Placebo | IM | 0 | 500 | 4 | 4 | 4 | 4 |
| 3 GAHB-Placebo | IN | 0 | 400 | 4 | 4 | 4 | 4 |
| 4 GAHB-Placebo | ID | 0 | 50 | 4 | 4 | 4 | 4 |
| 5 1790GAHB | IM | 6.1/100 | 500 | 4 | 4 | 4 | 4 |
| 6 1790GAHB | IN | 4.9/80 | 400 | 4 | 4 | 4 | 4 |
| 7 1790GAHB | ID | 0.61/10 | 50 | 4 | 4 | 4 | 4 |

Dosing days: 0, 14, 28 and 42.
[a]IM: intramuscular; IN: intranasal; ID: intradermal.
[b]Each animal in group 1 (control) received the sterile saline (0.9% NaCl) via all three routes.
[c]4 administrations of 100 μl per nostril 2 h apart, i.e. 400 μl/day. Nostrils were alternated between vaccinations.

Irwin Study in Rats with IN Vaccination

To further support IN administration of 1790GAHB, a GLP Irwin test was undertaken to identify potential undesired effects of 1790GAHB on the central and the peripheral nervous system as judged by a neurobehavioural observation battery [26]. Three groups of 6 male, approximately 0.3 kg, Han Wistar rats were used. The first group received saline control, the second GAHB-Placebo and the third 1790GAHB. Each rat received a single dose of 15 μl in each nostril (total of 30 μl). This volume administered was the maximum practical dose. The test group received 6 μg total of 1790GAHB protein. On a body weight basis, the 6 μg protein dose in a 0.3 kg rat is approximately 15 times the highest anticipated dose that would be administered IN to a 60 kg subject in the Phase 1 trial. Rats were monitored, prior to and at and 0.5, 1, 2, 5, and 24 hours post administration.

All animal studies complied with the EU Directive 2010/63 on the protection of animals for scientific purposes, and its implementation in the relevant local laws in Italy and France, respectively. The modified GMP pyrogenicity test was approved by the Charles River France Ethics Committee (Study numbers T 13.1446-48, T 13.1678-80, T 13.1702).

Results

O Antigen Expression of Shigella sonnei NVGH1790 Cell Line.

Strain NVGH1790 was genetically modified by the integration of E. coli nadA and nadB genes into the virulence plasmid to remove the nicotinic acid auxotrophy of Shigella [18]. Thus, retention of the virulence plasmid and consequently the production of the OAg encoded on the plasmid [27] is ensured by grow in medium without nicotinic acid. FACS analysis of S. sonnei NVGH1790 after 25 generations in flasks and after a 30 L fermentation showed that >95% of bacteria were positive for OAg thus showing retention of this plasmid.

Production at Pilot Scale and Characterization of 1790-GMMA

Three 30 L consistency runs were performed. For each batch, the fermentation process optimized at 30 L was stopped when the OD600 was approximately 35, within 20±4 hours from the inoculation of the bioreactor, when a dissolved $pO_2$ spike occurred and the pH started increasing. At the end of the fermentation, the culture was harvested by microfiltration. Subsequently, GMMA were purified by ultrafiltration. The process was transferred to an external Contract Manufacturing Organization for production of two GMP lots of 1790-GMMA. The GMP batch was produced at 25 L scale. Data are presented for one of the consistency lot produced at NVGH, 1790-GMMA batch NVGH1883 (reference batch), and for the two GMP drug substance, 1790-GMMA batch 1112 and batch 1014.

Yield and Characterization of GMMA

Size and Integrity

By electron microscopy, the purified GMMA from references and GMP batches showed particles with a bimodal size distribution. The majority of the particles are small with an average size of approximately 25-40 nm in diameter. A minor fraction of the particles was larger with sizes between 65 and 140 nm (16% of particles).

Dimensional analysis by Dynamic Light Scattering (DLS) using a Malvern Zetasizer Nano gave a Z-average 117 nm, 113 nm and 116 nm for the reference and the two GMP batches respectively. Results for polydispersion index 0.19, 0.21 and 0.20 were obtained for the reference and the two GMP batches, respectively. Importantly, DLS results were unaltered by multiple freeze thaw cycles or storage at −80° C. indicating that the GMMA remained intact and did not aggregate under these conditions. Thus, 1790-GMMA were routinely stored at −80° C. prior to formulation.

Yield

The reference and two GMP batches gave a final yield of 2.4 g protein (from 30 L), 1.7 g protein (from 25 L) and 0.42 g protein (from 25 L) in the purified GMMA, respectively. These lots contained 145 mg, 106 mg and 25 mg of OAg, respectively, with almost identical ratios of OAg to protein (60.3 μg/mg, 63.6 μg/mg and 59.0 μg/mg). The other two consistency lots (from 30 L) were similar: yield, 2.0 g and 3.2 g; OAg to protein ratio, 61.6 μg/mg and 50.3 μg/mg, respectively.

Protein Profile

The SDS-PAGE profile of 1790-GMMA proteins was similar to that seen in previous studies [22,36]. The dominant bands at approximately 39 kDa size were identified as OmpA and OmpC by mass spectrometry analysis.

LPS and O Antigen Profile

Silver stained SDS-PAGE of LPS extracted from reference and GMP batches showed an LPS ladder with a bimodal distribution (data not shown). The predominant bands were low molecular weight LPS with up to 5 OAg repeats; medium molecular weight LPS was visible as a minor fraction. These data were consistent with analytical size exclusion chromatography of extracted OAg/core using refractive index detection (data not shown). The dominant peak is low molecular weight polysaccharide. This size distribution of predominantly low molecular weight LPS in 1790-GMMA is markedly different to the size in the reference LPS derived from the parent strain without the LPS modification (1859-GMMA) that have an average of 33 repeats measured by NMR.

The composition of the LPS core was determined by HPAEC-PAD analysis. This method demonstrated that the molar ratio of galactose to glucose in the LPS present 1790-GMMA is 2:4, whereas in GMMA from the parent strain without the LPS modification (1859-GMMA) the ratio was 2:3 and similar to *S. sonnei* wild-type strains [22]. The change of glucose content in the LPS core of 1790-GMMA was confirmed by analysis of a third LPS core sugar, the terminal KDO. In 1790-GMMA and 1859-GMMA, the ratio of galactose to KDO was the same. The ratio of glucose to KDO differed confirming a higher glucose content in the LPS core of 1790-GMMA.

Lipid a Structure

The structure of the lipid A purified from the reference batch was determined by mass spectroscopy using MALDI-TOF (data not shown). The recorded spectra showed penta-acylated lipid A corresponding to the highest peak and several other peaks due to its fragmentation (i.e. loss of one or more fatty acid chains), aggregate formation with sodium (+23 m/z) and de-phosphorylation (−80 m/z). No hexa- or hepta-acylated lipid A was detected by MALDI-TOF.

IL-6 Production in MAT

1859-GMMA containing unmodified LPS induced high levels of IL-6 release from PBMC, causing a 10-fold increase in IL-6 release over background at a concentration of 0.004 ng protein/mL, whereas 1790-GMMA, containing penta-acylated LPS, needed a 600× higher concentration (2.37 ng protein/mL) to cause the same IL-6 release.

Intramuscular Pyrogenicity Test

The average temperature rises observed at the different intervals up to 7 h, and at 24 h after vaccination in all 12 rabbits receiving GMMA vaccines (6 in the first study receiving the toxicology lot, 3 in the second study receiving toxicology lot and 3 receiving the clinical lot) are shown in FIG. 1 compared to the average temperature rise of the 6 animals receiving saline. The average temperature rise in the vaccine group was still increasing at the normal 3 hour end point for an intravenous pyrogenicity test. After 5 h the average temperature rise in the control animals showed a significant increase and the difference between vaccine and control groups decreased. By 24 h the vaccine and control groups were not significantly different (vaccine group had a lower average temperature rise). Based on these results, 4 h was selected as the definitive time point. Using the criteria developed as detailed above, the toxicology and the two clinical vaccine groups passed the pyrogenicity test without requiring a repeat assay. The mean "maximum temperature rise" over the first 4 h after administration of the toxicology lot and the two clinical lots were 0.48° C., 0.53° C. and 0.40° C., respectively. For the control groups, the value was 0.27° C.

Toxicology Study

There was no mortality, no treatment-related clinical signs and no changes in body weight or food consumption in rabbits treated with 1790GAHB vaccine or GAHB-Placebo. There were no treatment-related ophthalmological findings. No organ weight changes considered to be related to either vaccine or placebo administration were noted at day 44 or at day 56 (i.e. 2 or 14 days after the final vaccination). The vaccine was locally well tolerated by intranasal and intramuscular routes with no observed local reaction by IN route and very slight (erythema, edema) up to moderate local reactions (edema) observed in some of the rabbits after IM administration. The ID administration induced very slight to moderate local reactions (induration, erythema and edema) which were more pronounced in the 1790GAHB group than in the corresponding GAHB-Placebo group. Local reactogenicity had completely or partially resolved by the end of the two-week recovery phase at the IM injection sites but not at the ID site of injection. However, the tolerability to the vaccine by ID administration remained acceptable. Inflammatory changes of low severity and magnitude including changes in draining lymph nodes and spleen were noted upon histopathologic examination; these changes correlated with increases in C-reactive protein and fibrinogen and were consistent with this pharmacological response to an immunogen. The changes in clinical pathology parameters and the minimal to moderate microscopic changes had generally resolved by the end of recovery phase in the groups treated IN and ID while those seen in the group treated IM had slightly decreased indicating recovery from inflammatory changes was ongoing.

There was a statistically significant increase in temperature in the rabbits receiving IM 1790GAHB compared to the IM placebo groups. This was only seen for the IM groups and mainly in males. After the first IM vaccination there was an average temperature rise of 0.43° C. for 1790 GABH vs 0.12° C. for placebo (p=0.009, t-test) at 2 hours and 0.64° C. for 1790GAHB vs 0.38° C. for placebo (p=0.005, t-test) at 6 h compared to pre-vaccination. At 24 h post injection, there was no difference in these groups (0.21 and 0.22° C. increases compared to the initial temperatures before vaccination, respectively). Similar temperature rises were seen in the IM groups following the 3rd and 4th injections (temperature increases of 0.44 vs 0.11 and 0.63 vs 0.33° C. at 6 h compared to pre-vaccination for 1790GAHB vs placebo). A smaller but statistically non-significant increase was seen following the second immunization (0.28 vs 0.14° C. at 6 h compared to pre-vaccination). While the differences were considered to be 1790GAHB-related, in view of the very low magnitude of the variation and the short period of increases, the effect was not considered to be toxicologically relevant.

Irwin Study

The Irwin study in rats to assess neurotoxic effects of IN vaccination following a single administration of 1790GAHB showed no relevant effects on a battery of behavioural and physiological parameters covering the main central and peripheral nervous system functions.

Immunogenicity and Potency in Mice

The initial immunogenicity study evaluated 7 different doses of 1790GAHB increasing 4-fold from 29 ng to 238 µg protein (1.75 ng to 14.35 µg of OAg) injected intraperitoneally and showed that the vaccine was highly immunogenic. Antibody was detectible at all doses after a single injection and was boosted following a second injection. 1.86 µg of protein (0.11 µg OAg) triggered the maximum antibody response. Based on these results, an immunogenicity protocol was developed to form the basis of potency tests and to assess stability over time as judged by potency. The final potency study design used four, 4-fold increasing doses of 1790GAHB from 29 ng to 1.86 µg of protein in groups of 8 mice with serum IgG levels assessed by ELISA on LPS with the homologous OAg three weeks after a single immunization. A reference 1790GAHB preparation was freshly formulated for each potency study, and administered at the same doses as the test vaccine. The dose-response curves of the antibody levels elicited by test vaccine and reference standard were compared. There was no significant difference in the slope or intercepts of the linear regression of the log transformed anti-LPS antibody on the log dose showing that the vaccine stability batch had the same potency as the freshly formulated reference material.

Immunogenicity in Rabbits

The IgG response in the rabbits from the toxicology study was assessed following each vaccination and at the final bleed. All three routes gave high levels of circulating anti-LPS IgG (data not shown). The maximum response had been achieved 14 days following a single IM injection of 100 µg dose of 1790GAHB. For the IN route, maximum antibody response took two immunizations. The circulating IgG anti-LPS levels 14 days after the final vaccination were not significantly different to the level achieved with IM delivery of the 100 µg dose of 1790GAHB. The 10 µg ID vaccination also gave an increase in response with subsequent vaccinations (Spearman rank test p<0.0001) but the effect was less pronounced than with the IN route. The final circulating anti-LPS IgG levels were significantly higher by the ID route than by the IM route (t test of log transformed antibody p=0.002)

Phase I Clinical Trial with *S. sonnei* 1790GAHB

This clinical trial was performed to evaluate the safety and immunogenicity of 3 doses of a candidate vaccine against *Shigella sonnei* (1790GAHB vaccine) when administered at different dosages in healthy adults (18 to 45 years of age at enrolment). The safety profile of the 1790GAHB vaccine is evaluated in comparison to that of placebo (GAHB-Placebo), constituted by an aluminium hydroxide suspension having the same concentration as study vaccine formulations. Subjects were randomized to receive three vaccinations, four weeks apart, of either 1790GAHB vaccine (at five antigen concentrations) or GAHB placebo.

Production Strain

*Shigella sonnei* containing the following genetic modifications: ΔtolR: breaks link between inner and outer membrane to give large quantity of outer membrane blebs (GMMA); ΔhtrB: to reduce reactogenicity of LPS; virG nadA/B knock-in: stabilizes virulence plasmid encoding O antigen (OAg)

Maximum Quantity Per 0.5 mL Dose (i.m.)
100 µg GMMA of protein
6.1 µg of OAg
0.35 mg aluminium as ALHYDROGEL®
In isotonic Tris buffered saline
Placebo per 0.5 mL dose (i.m.)
0.35 mg aluminium as ALHYDROGEL®
In isotonic Tris buffered saline
Lower doses for delivery prepared by diluting maximum dose in placebo
Injection volume: i.m: 0.5 mL

| Cohort | Route | Dose (OAg/Protein) | 1790GAHB # of Subjects | Placebo # of Subjects | Immunological Assessment |
|---|---|---|---|---|---|
| A | IM | 0.061/1 µg | 8 | 2 | Serum IgG |
| B | IM | 0.31/5 µg | 8 | 2 | |
| C | IM | 1.4/25 µg | 8 | 2 | |
| D | IM | 3.0/50 µg | 8 | 2 | |
| E | IM | 6.1/100 µg | 8 | 2 | |

Figure 2A:
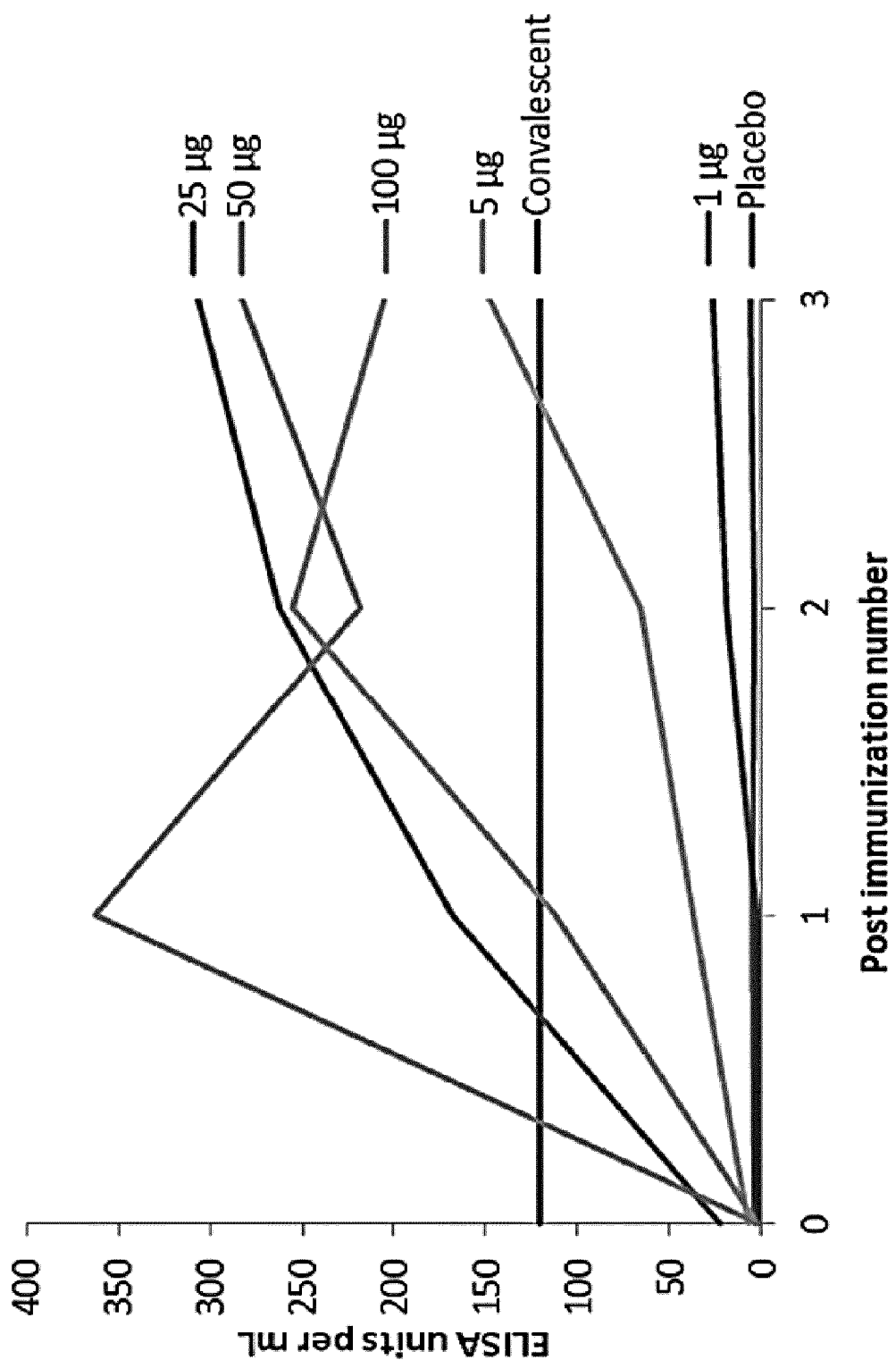
FIG. 2(A): Anti-*S. sonnei* LPS antibody levels (Median post-vaccination levels) generated post immunisation dose 1, 2 and 3 in a clinical trial with human subjects.
Figure 2B:
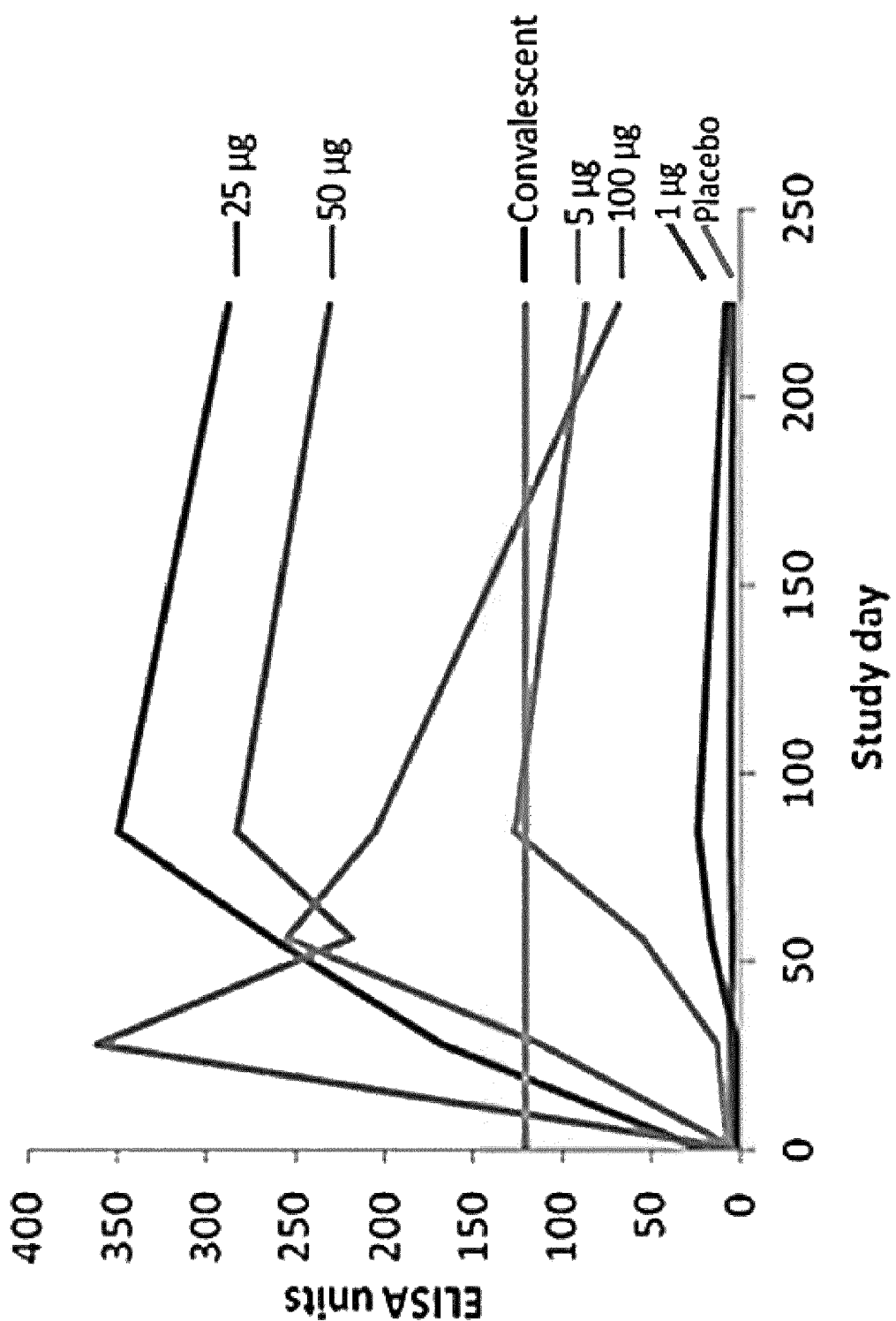
FIG. 2(B): Anti-*S. sonnei* LPS antibody levels (Median post-vaccination levels) over the entire study including 6 month follow up post immunisation 3 in a clinical trial with human subjects.

All doses of 1790GAHB were well tolerated and the safety data support use of ≤100 µg of 1790GAHB protein per dose when delivered by the IM route. Serologic assessment indicates sufficient serum IgG anti-*S. sonnei* LPS levels are elicited one month after the first, second and third vaccination in subjects receiving 25 µg, 50 µg and 100 µg of 1790GAHB (FIGS. 2(*a*) and (*b*)). The median level of antibody in these groups is greater than that observed in convalescent serum. These data support the use of 1790GAHB as a GMMA-based *S. sonnei* vaccine and a combination of four to six different GMMA in a multivalent formulation, assuming reactogenicity-immunogenicity profiles similar to 1790GAHB.

Multivalent *Shigella* Vaccine (I) Immunogenicity Assessment in Mice

In this study, a multivalent *Shigella* GMMA vaccine was tested, specifically an ALHYDROGEL® formulation containing GMMA from the 4 most prevalent serotypes of the GEMS study, *S. sonnei*, and *S. flexneri* 2a, 3a, and 6.

For this purpose, GMMA production of the *S. flexneri* strains was enhanced by tolR deletion as in *S. sonnei* and the reactogenicity of the LPS was reduced by genetic modification of the lipid A through deletion of the htrB gene. An ALHYDROGEL® formulation was chosen for the 4-valent formulation and the single GMMA formulations based on the experience with 1790GAHB in rabbits that adsorption to aluminium hydroxide enhances tolerability. This study was the first immunogenicity study for the *S. flexneri* serotypes.

GEL® Diluent Placebo contained: ALHYDROGEL® in Tris-buffered saline at the same concentrations as in 1790GAHB (ALHYDROGEL® 0.7 mg A13+/mL, 10 mM Tris, pH 7.4, 9 g/L sodium chloride).

Immunization

BALB/c mice (8 per group) were immunized intraperitoneally on day 0 with 4 different doses of the formulations, as described in the table below. One group was immunized with ALHYDROGEL® diluent (GAHB-Placebo) as control. All formulations were tested for bacterial contamination before immunization. Briefly, 50 µL of each formulation were plated on LB agar plates in triplicate and after 24 h incubation at 37° C. plates were examined for growth. Only formulations with no bacterial growth were used for immunization.

| Group # | Mice # | Antigen Name | Antigen Dosage (in protein) | Adjuvant (0.35 mg $Al_{3+}$ per dose) | VPA | Route |
|---|---|---|---|---|---|---|
| 1 | 1-8 | *S. sonnei* (1790GAHB) | 2 ng | Alhydrogel | 500 µL | IP |
| 2 | 9-16 | *S. flexneri* 2a | 2 ng | Alhydrogel | 500 µL | IP |
| 3 | 17-24 | *S. flexneri* 3a | 2 ng | Alhydrogel | 500 µL | IP |
| 4 | 25-32 | *S. flexneri* 6 | 2 ng | Alhydrogel | 500 µL | IP |
| 5 | 33-40 | 4-valent Combination | 8 ng | Alhydrogel | 500 µL | IP |
| 6 | 41-48 | *S. sonnei* (1790GAHB) | 20 ng | Alhydrogel | 500 µL | IP |
| 7 | 49-56 | *S. flexneri* 2a | 20 ng | Alhydrogel | 500 µL | IP |
| 8 | 57-64 | *S. flexneri* 3a | 20 ng | Alhydrogel | 500 µL | IP |
| 9 | 65-72 | *S. flexneri* 6 | 20 ng | Alhydrogel | 500 µL | IP |
| 10 | 73-80 | 4-valent Combination | 80 ng | Alhydrogel | 500 µL | IP |
| 11 | 81-88 | *S. sonnei* (1790GAHB) | 200 ng | Alhydrogel | 500 µL | IP |
| 12 | 89-96 | *S. flexneri* 2a | 200 ng | Alhydrogel | 500 µL | IP |
| 13 | 97-104 | *S. flexneri* 3a | 200 ng | Alhydrogel | 500 µL | IP |
| 14 | 105-112 | *S. flexneri* 6 | 200 ng | Alhydrogel | 500 µL | IP |
| 15 | 113-120 | 4-valent Combination | 800 ng | Alhydrogel | 500 µL | IP |
| 16 | 121-128 | *S. sonnei* (1790GAHB) | 2000 ng | Alhydrogel | 500 µL | IP |
| 17 | 129-136 | *S. flexneri* 2a | 2000 ng | Alhydrogel | 500 µL | IP |
| 18 | 137-144 | *S. flexneri* 3a | 2000 ng | Alhydrogel | 500 µL | IP |
| 19 | 145-152 | *S. flexneri* 6 | 2000 ng | Alhydrogel | 500 µL | IP |
| 20 | 153-160 | 4-valent Combination | 8000 ng | Alhydrogel | 500 µL | IP |
| 21 | 161-168 | GAHB-Placebo | — | Alhydrogel | 500 µL | IP |

Figure 3:
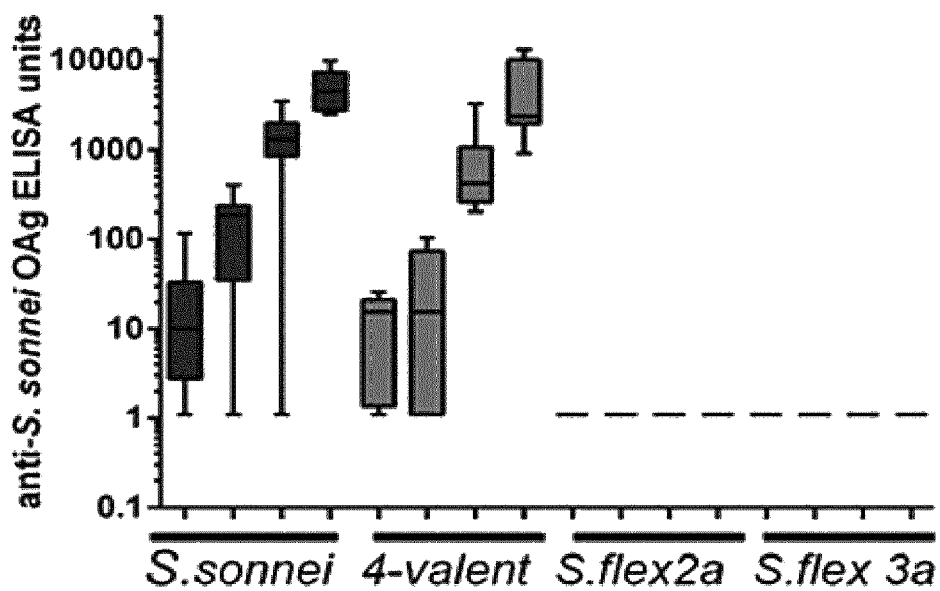
FIG. 3: Box plots showing the antibody distribution in groups immunized with 1790GAHB, *S. flexneri*-2a, *S. flexneri*-3a and 4-valent Combination assessed by ELISA using LPS purified from (A) *S. sonnei*, (B) *S. flexneri* 3a, and (C) *S. flexneri* 2a as coating antigen. In (A) and (B) ELISA units are plotted, in (C) the ELISA ODs are shown. The 25th to 75th percentile is shown as the rectangle, the minimum and maximum values as whiskers and the median as the horizontal bar in the rectangle. The detection limits in the assays were 2.2 (A) and 1.6 (B) ELISA units. Results below the detection limit were assigned the value of half of the detection limit (1.1 in A, 0.8 in B). The average background OD in the assays shown in (C) was 0.056.
Figure 3:
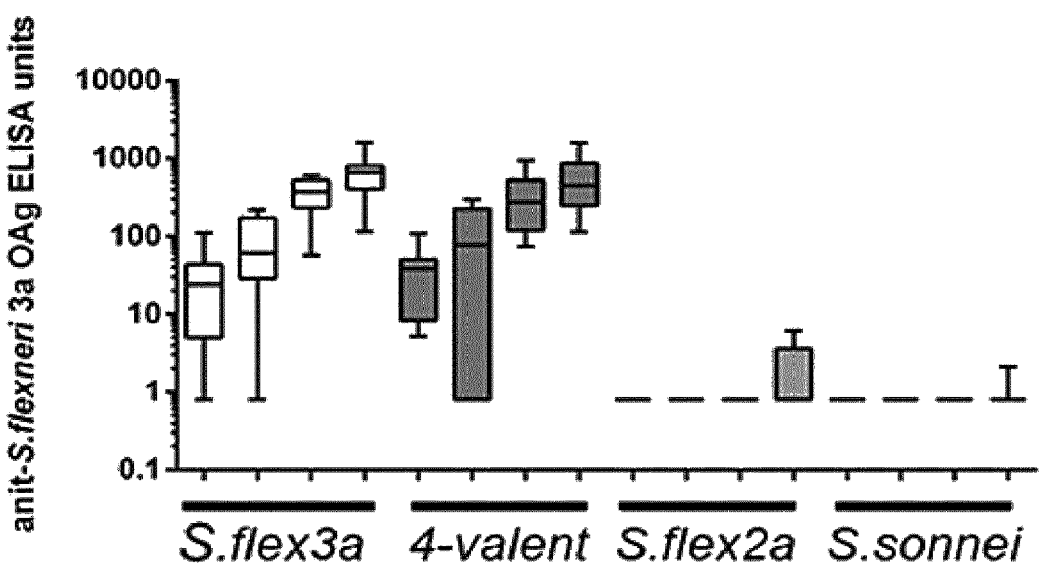
Figure 3:
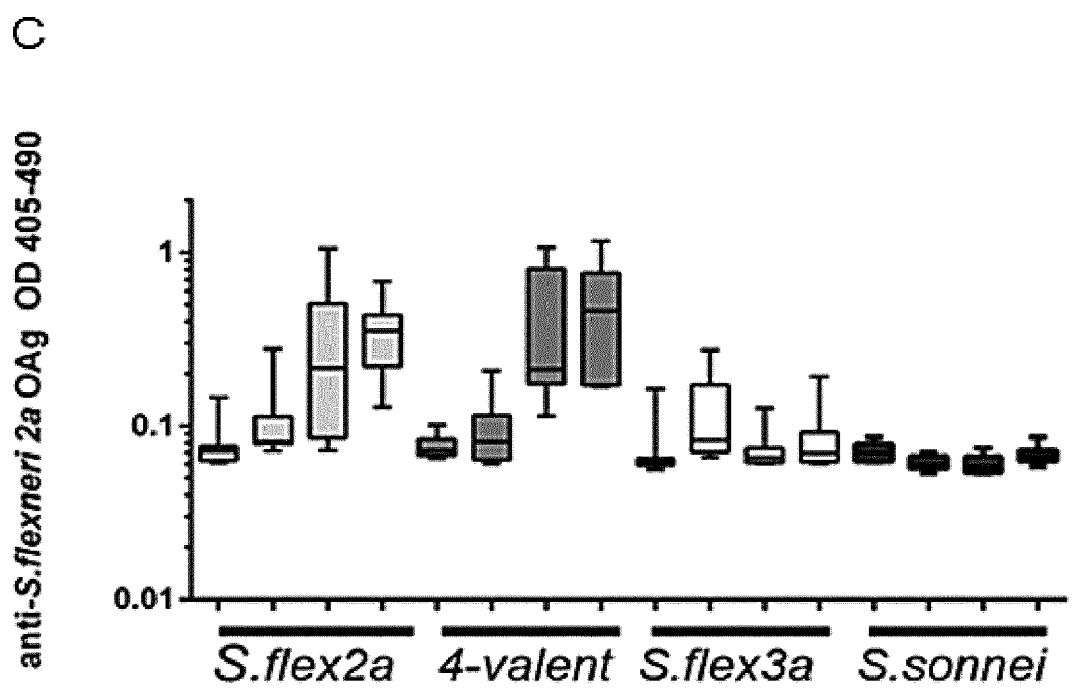
Figure 4:
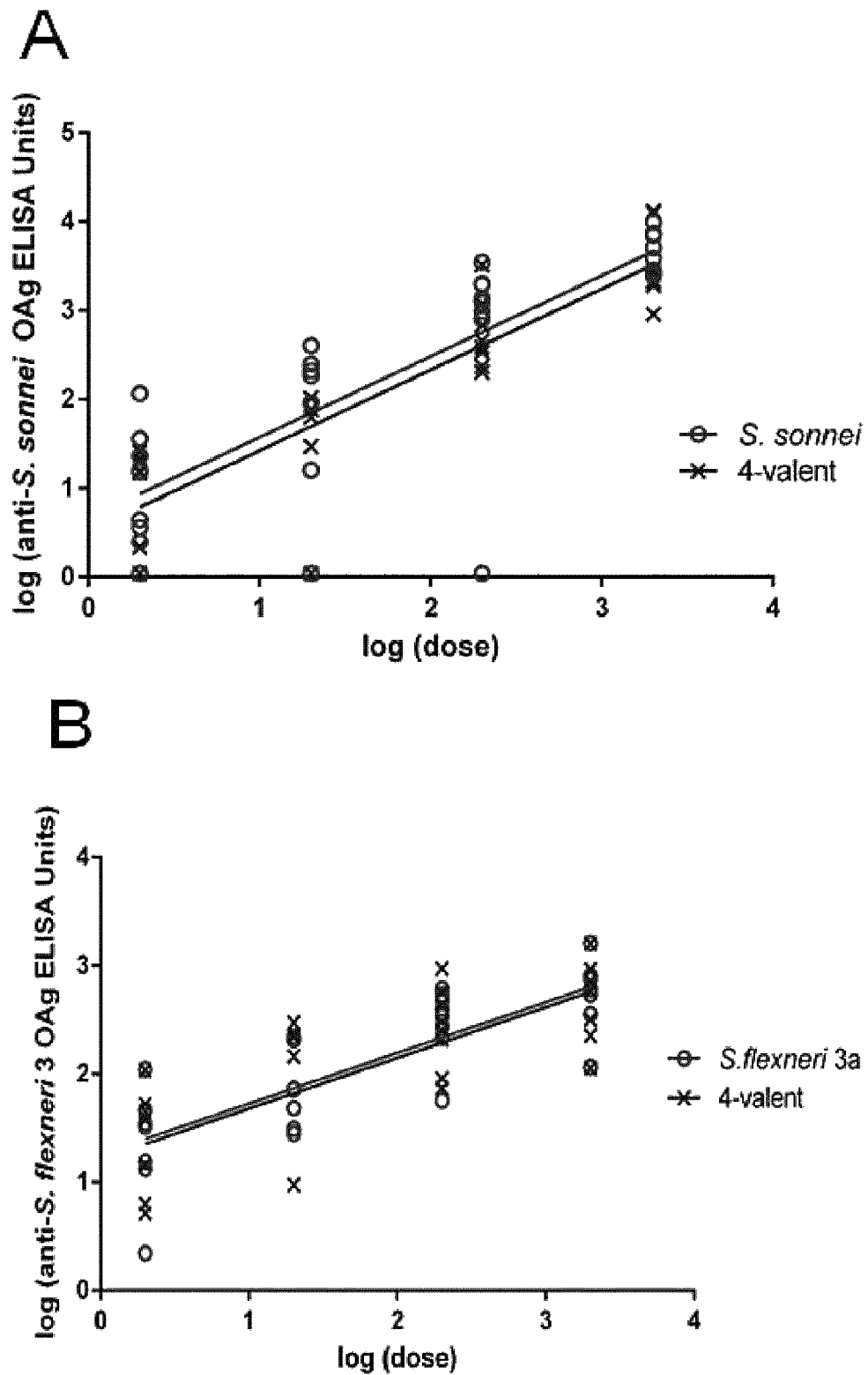
FIG. 4: Scatter plots showing the log-transformed individual results of the anti-*S. sonnei* OAg (A), anti-*S. flexneri* 3a (B) or the ELISA OD results of anti-*S. flexneri* 2a (C) antibody distribution in each group versus the log-transformed dosages. Parallel dose-response curves of the single formulations and the 4-valent formulation are shown. (A) Dose-response curves for 1790GAHB and 4-valent Combination on LPS from *S. sonnei*. (B) Dose-response curves *S. flexneri* 3a and 4-valent Combination on LPS from *S. flexneri* 3a. (C) Dose-response curves for *S. flexneri* 2a and 4-valent Combination on LPS from *S. flexneri* 2a. The Y intercepts of the curves are not significantly different, P=0.31 (A), P=0.74 (B), P=0.75 (C).
Figure 4:
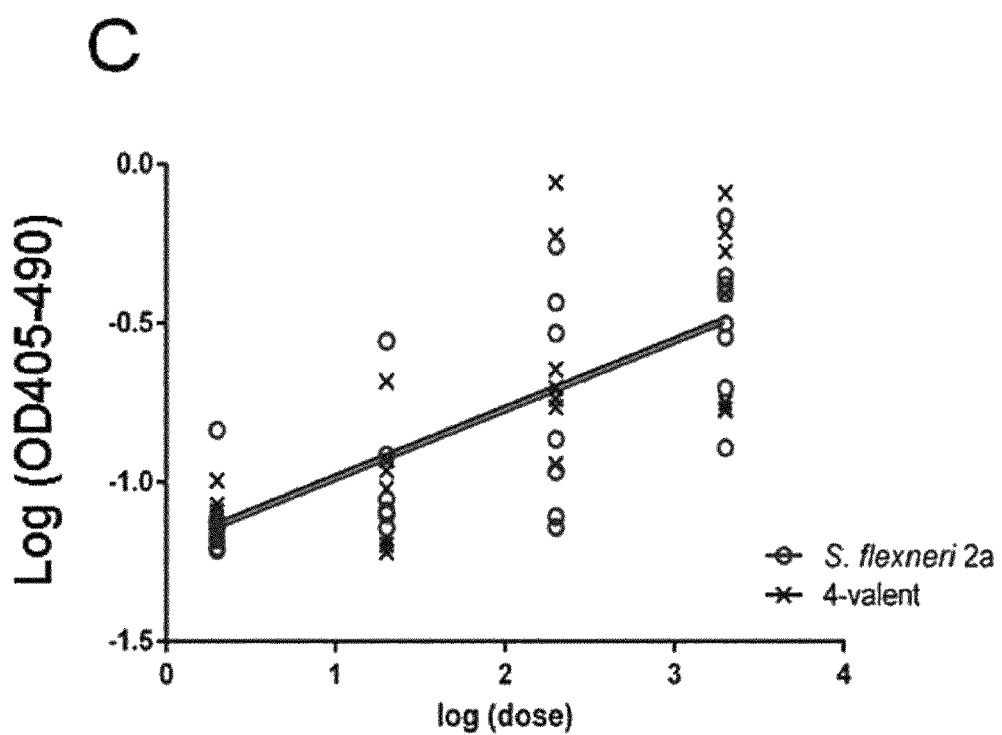

Blood draw for serology: Blood was obtained on day 21 from all animals, the sera were collected and sera were stored at 2-8° C. until tested.
ELISA
ELISAs were performed to determine the anti-*S. sonnei* LPS, anti-*S. flexneri* 2a OAg, anti-*S. flexneri* 3a OAg, anti-*S. flexneri* 6 OAg antibodies levels of mice immunized respectively with ALHYDROGEL® formulated GMMA from *S. sonnei*, *S. flexneri* 2a, *S. flexneri* 3a and *S. flexneri* 6 administered alone or as a part of a 4-valent vaccine. Results for *S. sonnei*, *S. flexneri* 2a and *S. flexneri* 3a are shown in FIGS. 3 and 4.

Formulations were prepared based on protein content as used for 1790GAHB. Based on biochemical characterization, *S. flexneri* 2a GMMA contain approximately 10 times more OAg per mg of protein than 1790-GMMA. Thus, a 10-fold lower starting concentration than in regular 1790GAHB potency study (29 ng, see above) was chosen. Similar dosing was established for *S. flexneri* 3a GMMA and *S. flexneri* 6 GMMA. The OAg response to single GMMA formulation (*S. sonnei* or *S. flexneri* 2a, 3a or 6) was compared to the response to the same OAg elicited by the 4-valent formulation. Strong immunogenicity of all components included in the 4-valent formulation will provide proof of concept of immunogenicity for a multivalent formulation and support further development of a multivalent OAg-GMMA formulation.

In the 4-valent formulation, each of the components is present at the same concentration as in the single formulations described previously. Thus, the total protein content of the 4-valent formulation is 160 µg/mL. For the 4-valent formulation the *S. sonnei* GMMA, *S. flexneri* 2a GMMA, *S. flexneri* 3a GMMA and *S. flexneri* 6 GMMA are mixed at the same concentrations then formulated with aluminium hydroxide as specified above. The GAHB ALHYDRO- Mice immunized with increasing concentrations of 1790GAHB and raised a specific anti-*S. sonnei* LPS antibodies (measured in ELISA units) that gave a significant Spearman rank with P<0.0001 (alpha=0.05) and a correlation coefficient of 0.86, mice immunized with increasing concentrations of the 4-valent formulation raised specific anti-*S. sonnei* LPS antibodies (measured in ELISA units) with a significant Spearman rank with P<0.0001 (alpha=0.05) and a correlation coefficient of 0.86.

Mice immunized with increasing concentrations of *S. flexneri* 3a raised specific anti-*S. flexneri* 3a OAg antibodies and a significant Spearman rank with P<0.0001 (alpha=0.05) and a correlation coefficient of 0.84. Similarly, mice immunized with increasing concentrations of the 4-valent formulation raised specific anti-*S. flexneri* 3a OAg antibodies with a significant Spearman rank with P<0.0001 (alpha=0.05) and a correlation coefficient of 0.73. The anti-*S. flexneri* 2a OAg ELISA OD obtained with sera from mice immunized with increasing concentrations of *S. flexneri* 2a gave a significant Spearman rank with P<0.0001 (alpha=0.05) and a correlation coefficient of 0.75. Also mice immunized with increasing concentrations of the 4-valent formulation raised anti-*S. flexneri* 2a OAg antibodies that had significant Spearman rank with P<0.0001 (alpha=0.05) and a correlation coefficient of 0.75. The results of the respective dose-response curve comparisons are shown in FIG. 4. No significant differences between were observed for any serovar specific response between the single GMMA formulation and the 4-valent formulation indicating that there was no interference.

FACS Analysis

Antisera generated against the 4-valent GMMA formulation recognized wild-type *S. sonnei*, *S. flexneri* 2a, *S. flexneri* 3a and *S. flexneri* 6. Whereas individual GMMA antisera recognized the homologous bacterial strain.

CONCLUSIONS

The serum antibody response to the specific *Shigella* serovar elicited by the 4-valent *Shigella* formulation was not different from the individual components. Thus, there is no evidence of interference.

Multivalent *Shigella* Vaccine (II)

A multivalent *Shigella* GMMA vaccine is exemplified, specifically an ALHYDROGEL® formulation containing GMMA from *S. sonnei*, and *S. flexneri* 1b, 2a, 3a, and 6.

GMMA production of the *S. flexneri* strains is enhanced by tolR deletion as in *S. sonnei* and the reactogenicity of the LPS is reduced by genetic modification of the lipid A through deletion of either the msbB or htrB gene. As before, an ALHYDROGEL® formulation is chosen for the 5-valent formulation and the single GMMA formulations based on the experience with 1790GAHB in rabbits that adsorption to aluminium hydroxide enhances tolerability.

In the 5-valent formulation, each of the components is present at the same concentration as in the single formulations described previously. For the 5-valent formulation the *S. sonnei* GMMA, *S. flexneri* 1b GMMA, *S. flexneri* 2a GMMA, *S. flexneri* 3a GMMA and *S. flexneri* 6 GMMA are mixed at the same concentrations then formulated with aluminium hydroxide as specified above.

Multivalent *Shigella* Vaccine (III)

A multivalent *Shigella* GMMA vaccine is exemplified, specifically an ALHYDROGEL® formulation containing GMMA from *S. sonnei*, and *S. flexneri* 1b, 2a, 2b, 3a, and 6.

GMMA production of the *S. flexneri* strains is enhanced by tolR deletion as in *S. sonnei* and the reactogenicity of the LPS is reduced by genetic modification of the lipid A through deletion of either the msbB or htrB gene. As before, an ALHYDROGEL® formulation is chosen for the 6-valent formulation and the single GMMA formulations based on the experience with 1790GAHB in rabbits that adsorption to aluminium hydroxide enhances tolerability.

In the 6-valent formulation, each of the components is present at the same protein or O-antigen concentration as in the single formulations described previously. For the 6-valent formulation the *S. sonnei* GMMA, *S. flexneri* 1b GMMA, *S. flexneri* 2a GMMA, *S. flexneri* 2b GMMA, *S. flexneri* 3a GMMA and *S. flexneri* 6 GMMA are mixed at the same concentrations then formulated with aluminium hydroxide as specified above.

Specific Combinations

A) An immunogenic composition comprising (a) GMMA purified from a *Shigella sonnei* 53G ΔtolR, ΔhtrB, virG::nadAB mutant, (b) GMMA purified from a *Shigella flexneri* 2a 2457T ΔtolR, ΔmsbB1 mutant, (c) GMMA purified from a *Shigella flexneri* 3a 6885 ΔtolR, ΔmsbB1 mutant, (d) GMMA purified from a *Shigella flexneri* 6 10.8537 ΔtolR, ΔhtrB ΔmsbB1 mutant and (e) an aluminium adjuvant, wherein the GMMA comprise modified lipid A and wherein the *Shigella flexneri* strains are cured of the virulence plasmid.

B) An immunogenic composition comprising (a) GMMA purified from a *Shigella sonnei* 53G ΔtolR, ΔhtrB, virG::nadAB mutant, (b) GMMA purified from a *Shigella flexneri* 2a 2457T ΔtolR, ΔmsbB1 mutant, (c) GMMA purified from a *Shigella flexneri* 3a 6885 ΔtolR, ΔmsbB1 mutant, (d) GMMA purified from a *Shigella flexneri* 6 10.8537 ΔtolR, ΔmsbB1 mutant, (e) GMMA purified from a *Shigella flexneri* 1b STANSFIELD ΔtolR, ΔmsbB1 mutant and (f) an aluminium adjuvant, wherein the GMMA comprise modified lipid A and wherein the *Shigella flexneri* strains are cured of the virulence plasmid.

C) An immunogenic composition comprising (a) GMMA purified from a *Shigella sonnei* 53G ΔtolR, ΔhtrB, virG::nadAB mutant, (b) GMMA purified from a *Shigella flexneri* 2a 2457T ΔtolR, ΔmsbB1 mutant, (c) GMMA purified from a *Shigella flexneri* 3a 6885 ΔtolR, ΔmsbB1 mutant, (d) GMMA purified from a *Shigella flexneri* 6 10.8537 ΔtolR, ΔmsbB1 mutant, (e) GMMA purified from a *Shigella flexneri* 2b 69/50 ΔtolR, ΔmsbB1 mutant and (f) an aluminium adjuvant, wherein the GMMA comprise modified lipid A and wherein the *Shigella flexneri* strains are cured of the virulence plasmid.

D) An immunogenic composition comprising (a) GMMA purified from a *Shigella sonnei* 53G ΔtolR, ΔhtrB, virG::nadAB mutant, (b) GMMA purified from a *Shigella flexneri* 2a 2457T ΔtolR, ΔmsbB1 mutant, (c) GMMA purified from a *Shigella flexneri* 3a 6885 ΔtolR, ΔmsbB1 mutant, (d) GMMA purified from a *Shigella flexneri* 6 10.8537 ΔtolR, ΔmsbB1 mutant, (e) GMMA purified from a *Shigella flexneri* 1b STANSFIELD ΔtolR, ΔmsbB1 mutant, (0 GMMA purified from a *Shigella flexneri* 2b 69/50 ΔtolR, ΔmsbB1 mutant and (g) an aluminium adjuvant, wherein the GMMA comprise modified lipid A and wherein the *Shigella flexneri* strains are cured of the virulence plasmid.

E) The immunogenic composition of (A), (B), (C) or (D) wherein the adjuvant is aluminium hydroxide, for example, ALHYDROGEL®.

F) The immunogenic composition of any of (A), (B), (C), (D) or (E) which comprises at least one pharmaceutical carrier(s) and/or excipients.

G) The immunogenic composition of F which is a pharmaceutical or vaccine composition.

H) The pharmaceutical or vaccine composition of G for use in prevention or treatment of infection by *Shigella* in an animal, particularly a human.

While certain embodiments of the present invention have been described and specifically exemplified above, it is not intended that the invention be limited to such embodiments. Various modifications may be made thereto without departing from the scope and spirit of the present invention as set forth in the following claims.

REFERENCES

1. Murray C J, Vos T, Lozano R, Naghavi M, Flaxman A D, Michaud C, et al. Disability-adjusted life years (DALYs) for 291 diseases and injuries in 21 regions, 1990-2010: a systematic analysis for the Global Burden of Disease Study 2010. Lancet. 2012; 380: 2197-2223.

2. Lozano R, Naghavi M, Foreman K, Lim S, Shibuya K, Aboyans V, et al. Global and regional mortality from 235 causes of death for 20 age groups in 1990 and 2010: a systematic analysis for the Global Burden of Disease Study 2010. Lancet. 2012; 380: 2095-2128.
3. Kotloff K L, Nataro J P, Blackwelder W C, Nasrin D, Farag T H, Panchalingam S, et al. Burden and aetiology of diarrhoeal disease in infants and young children in developing countries (the Global Enteric Multicenter Study, GEMS): a prospective, case-control study. Lancet. 2013; 382: 209-222.
4. Livio S, Strockbine N A, Panchalingam S, Tennant S M, Barry E M, Marohn M E, et al. *Shigella* isolates from the global enteric multicenter study inform vaccine development. Clin Infect Dis. 2014; 59: 933-941.
5. Levine M M, Kotloff K L, Barry E M, Pasetti M F, Sztein M B. Clinical trials of *Shigella* vaccines: two steps forward and one step back on a long, hard road. Nat Rev Microbiol. 2007; 5: 540-553.
6. Chang Z, Lu S, Chen L, Jin Q, Yang J. Causative species and serotypes of shigellosis in mainland China: systematic review and meta-analysis. PLoS One. 2012; 7: e52515.
7. Vinh H, Nhu N T K, Nga T V T, Duy P T, Campbell J I, Hoang N V M, et al. A changing picture of shigellosis in southern Vietnam: shifting species dominance, antimicrobial susceptibility and clinical presentation. BMC Infect Dis. 2009; 9: 204.
8. Kweon, 2008 Curr Opin Infect Dis. 21(3):313-8.
9. Cohen D, Ashkenazi S, Green M S, Gdalevich M, Robin G, Slepon R, et al. Double-blind vaccine-controlled randomised efficacy trial of an investigational *Shigella sonnei* conjugate vaccine in young adults. Lancet. 1997; 349: 155-159.
10. Passwell J H, Ashkenzi S, Banet-Levi Y, Ramon-Saraf R, Farzam N, Lerner-Geva L, et al. Age-related efficacy of *Shigella* O-specific polysaccharide conjugates in 1-4-year-old Israeli children. Vaccine. 2010; 28: 2231-2235.
11. Susanna Esposito, Roman Prymula, Gian Vincenzo Zuccotti, Fang Xie, Michelangelo Barone, Peter M Dull, Daniela Toneatto, A phase II randomized controlled trial of a multicomponent meningococcal serogroup B vaccine, 4CMenB, in infants (II). Human Vaccines & Immunotherapeutics Vol. 10, Iss. 7, 2014.
12. Erlandson and Mackey (1958) J Bacteriol 75(3): 253-7.
13. U.S. Pat. No. 5,681,736.
14. Uyttendaele et al. (2001) International journal of food microbiology 70(3):255-65.
15. Formal S B, Kent T H, May H C, Palmer A, Falkow S, LaBrec E H. Protection of monkeys against experimental shigellosis with a living attenuated oral polyvalent dysentery vaccine. J Bacteriol. 1966; 92: 17-22.
16. Makino S, Sasakawa C, Kamata K, Kurata T, Yoshikawa M. A genetic determinant required for continuous reinfection of adjacent cells on large plasmid in *S. flexneri* 2a. Cell. 1986; 46: 551-555.
17. Berlanda Scorza F, Colucci A M, Maggiore L, Sanzone S, Rossi O, Ferlenghi I, et al. High yield production process for *Shigella* outer membrane particles. PLoS One. 2012; 7: e35616.
18. Prunier A-L, Schuch R, Fernandez R E, Mumy K L, Kohler H, McCormick B A, et al. nadA and nadB of *Shigella flexneri* 5a are antivirulence loci responsible for the synthesis of quinolinate, a small molecule inhibitor of *Shigella* pathogenicity. Microbiology. 2007; 153: 2363-2372.
19. Clementz T, Bednarski J J, Raetz C R. Function of the htrB high temperature requirement gene of *Escherchia coli* in the acylation of lipid A. J Biol Chem. 1996; 271: 12095-12102.
20. Rossi O, Pesce I, Giannelli C, Aprea S, Caboni M, Citiulo F, et al. Modulation of Endotoxicity of *Shigella* Generalized Modules for Membrane Antigens (GMMA) by Genetic Lipid A Modifications: Relative Activation of TLR4 and TLR2 Pathways in Different Mutants. J Biol Chem. 2014; 289: 24922-24935.
21. Micoli F, Rondini S, Gavini M, Pisoni I, Lanzilao L, Colucci A M, et al. A scalable method for O-antigen purification applied to various *Salmonella* serovars. Anal Biochem. 2013; 434: 136-145.
22. Robbins J B, Kubler-Kielb J, Vinogradov E, Mocca C, Pozsgay V, Shiloach J, et al. Synthesis, characterization, and immunogenicity in mice of *Shigella sonnei* 0-specific oligosaccharide-core-protein conjugates. Proc Natl Acad Sci USA. 2009; 106: 7974-7978.
23. Westphal O, Jann K. Bacterial lipopolysaccharides: extraction with phenol-water and further application of the procedure. 1965; 5: 83-91.
24. Stoddard M B, Pinto V, Keiser P B, Zollinger W. Evaluation of a whole-blood cytokine release assay for use in measuring endotoxin activity of group B *Neisseria meningitidis* vaccines made from lipid A acylation mutants. Clin Vaccine Immunol. 2010; 17: 98-107.
25. Pyrogens. In: European Pharmacopoeia. 8th ed. Strasbourg, Cedex: Directorate for the Quality of Medicines & HealthCare of the Council of Europe (EDQM). 2013. chapter 2.6.8.
26. Moscardo E, Maurin A, Dorigatti R, Champeroux P, Richard S. An optimised methodology for the neurobehavioural assessment in rodents. J Pharmacol Toxicol Methods. 2007; 56: 239-255.
27. Jiang Y, Yang F, Zhang X, Yang J, Chen L, Yan Y, et al. The complete sequence and analysis of the large virulence plasmid pSS of *Shigella sonnei*. Plasmid. 2005; 54: 149-159.
28. Rossi O, Maggiore L, Necchi F, Koeberling O, MacLennan C A, Saul A, et al. Comparison of Colorimetric Assays with Quantitative Amino Acid Analysis for Protein Quantification of Generalized Modules for Membrane Antigens (GMMA). Mol Biotechnol. 2014; in press.
29. [A]. Maggiore L, Yu L, Omasits U, Rossi O, Dougan G, Thomson N R, Saul A, Choudhary J S, Gerke C. Quantitative proteomic analysis of *Shigella flexneri* and *Shigella sonnei* Generalized Modules for Membrane Antigens (GMMA) reveals highly pure preparations. Int J Med Microbiol. 2016 February; 306(2):99-108
30. [B]. Christiane Gerke, Anna Maria Colucci, Carlo Giannelli, Silvia Sanzone, Claudia Giorgina Vitali, Luigi Sollai, Omar Rossi, Laura B. Martin, Jochen Auerbach, Vito Di Cioccio, Allan Saul. Production of a *Shigella sonnei* Vaccine Based on Generalized Modules for Membrane Antigens (GMMA), 1790GAHB.
31. PLoS One. 2015; 10(8): e013447831. Zhu D, Huang S, Gebregeorgis E, McClellan H, Dai W, Miller L, Saul A. Development of a Direct ALHYDROGEL® Formulation Immunoassay (DAFIA). J Immunol Methods. 2009 May 15; 344(1):73-8
32. Datsenko et al. (Proc Natl Acad Sci USA. 2000 Jun. 6; 97(12):6640-5.

The invention claimed is:

1. An immunogenic composition comprising:
   (a) purified *Shigella sonnei* Generalized Modules for Membrane Antigens (GMMA) purified from at least one strain selected from the group consisting of
      (i) *Shigella sonnei* ΔtolR, ΔhtrB, ΔvirG::nadAB,
      (ii) *Shigella sonnei* ΔtolR, ΔmsbB1, ΔvirG::nadAB,
      (iii) *Shigella sonnei* ΔtolR, ΔmsbB2, ΔvirG::nadAB, and
      (iv) *Shigella sonnei* ΔtolR, ΔmsbB1 ΔmsbB2, ΔvirG::nadAB,
   (b) purified *Shigella flexneri* GMMA purified from at least one strain selected from the group consisting of
      (i) *Shigella flexneri* 2a ΔtolR, ΔmsbB,
      (ii) *Shigella flexneri* 2a ΔtolR, ΔhtrB,
      (iii) *Shigella flexneri* 3a ΔtolR, ΔmsbB,
      (iv) *Shigella flexneri* 3a ΔtolR, ΔhtrB,
      (v) *Shigella flexneri* 3a ΔtolR, ΔmsbB, and
      (vi) *Shigella flexneri* 3a ΔtolR, ΔhtrB, and
   (c) an aluminum adjuvant.

2. The immunogenic composition of claim 1 wherein the immunogenic composition comprises *Shigella flexneri* GMMA purified from each of strains 2a and 3a.

3. The immunogenic composition of claim 2 wherein the GMMA are purified from (a) *Shigella sonnei* ΔtolR, ΔhtrB, virG::nadAB, (b) *Shigella flexneri* 2a ΔtolR, ΔmsbB or *Shigella flexneri* 2a ΔtolR, ΔhtrB and (c) *Shigella flexneri* 3a ΔtolR, ΔmsbB or *Shigella flexneri* 3a ΔtolR, ΔhtrB.

4. The immunogenic composition of claim 1 wherein the *S. sonnei* strain is *S. sonnei* 53G.

5. The immunogenic composition of claim 1 wherein the *S. flexneri* strain(s) are selected from the group consisting of *S. flexneri* 2457T (2a); and *S. flexneri* 6885 (3a).

6. The immunogenic composition of claim 1 wherein the composition further comprises purified *Shigella flexneri* GMMA purified from at least one further *Shigella flexneri* strain selected from the group consisting of 1b and 2b.

7. The immunogenic composition of claim 6 wherein the further *Shigella flexneri* strain(s) are selected from the group consisting of *S. flexneri* STANSFIELD (serotype 1b) and *S. flexneri* 69/50 (serotype 2b).

8. The immunogenic composition of claim 1 wherein the adjuvant is aluminum hydroxide.

9. The immunogenic composition of claim 1 wherein at least 75% of the GMMA have a diameter within the range of 25 nm to 40 nm.

10. The immunogenic composition of claim 1 which further comprises at least one pharmaceutical carrier(s) and/or excipients.

11. The immunogenic composition of claim 10 which is a pharmaceutical or vaccine composition.

12. A method of generating an immune response to *Shigella* comprising the step of administering to a patient the composition of claim 11.

* * * * *

SEQUENCE LISTING

<160> NUMBER OF SEQ ID NOS: 67

<210> SEQ ID NO 1
<211> LENGTH: 36
<212> TYPE: DNA
<213> ORGANISM: Artificial
<220> FEATURE:
<223> OTHER INFORMATION: Shigella sonnei

<400> SEQUENCE: 1
actcgagctc tgtagttgat ttgacagttg acatcc                                  36

<210> SEQ ID NO 2
<211> LENGTH: 41
<212> TYPE: DNA
<213> ORGANISM: Artificial
<220> FEATURE:
<223> OTHER INFORMATION: Shigella sonnei

<400> SEQUENCE: 2
ctaacccggg cactatatta tcagtaagtg gttgataaac c                            41

<210> SEQ ID NO 3
<211> LENGTH: 26
<212> TYPE: DNA
<213> ORGANISM: Artificial
<220> FEATURE:
<223> OTHER INFORMATION: Shigella sonnei

<400> SEQUENCE: 3
ctaacccggg cgtgttgatg tcctgc                                             26

<210> SEQ ID NO 4
<211> LENGTH: 31
<212> TYPE: DNA
<213> ORGANISM: Artificial
<220> FEATURE:
<223> OTHER INFORMATION: Shigella sonnei

<400> SEQUENCE: 4
acgcgtcgac agttcagttc aggctgtacg c                                       31

<210> SEQ ID NO 5
<211> LENGTH: 34
<212> TYPE: DNA
<213> ORGANISM: Artificial
<220> FEATURE:
<223> OTHER INFORMATION: Shigella sonnei

<400> SEQUENCE: 5
ctaacccggg caagcaactc tatgtcggtg gaat                                    34

<210> SEQ ID NO 6
<211> LENGTH: 29
<212> TYPE: DNA
<213> ORGANISM: Artificial
<220> FEATURE:
<223> OTHER INFORMATION: Shigella sonnei

<400> SEQUENCE: 6
tatcaagctt ggcaaggcca atacacagc                                          29

<210> SEQ ID NO 7
<211> LENGTH: 35
<212> TYPE: DNA
<213> ORGANISM: Artificial

```
<220> FEATURE:
<223> OTHER INFORMATION: Shigella sonnei

<400> SEQUENCE: 7
tatcaagctt agggttagag tgtctcgttt ttgta                           35

<210> SEQ ID NO 8
<211> LENGTH: 28
<212> TYPE: DNA
<213> ORGANISM: Artificial
<220> FEATURE:
<223> OTHER INFORMATION: Shigella sonnei

<400> SEQUENCE: 8
ctaacccggg ccagaccaga actattcc                                  28

<210> SEQ ID NO 9
<211> LENGTH: 36
<212> TYPE: DNA
<213> ORGANISM: Artificial
<220> FEATURE:
<223> OTHER INFORMATION: Shigella flexneri

<400> SEQUENCE: 9
ctagtctaga aacccgggca attgtatgta ttgtcg                         36

<210> SEQ ID NO 10
<211> LENGTH: 27
<212> TYPE: DNA
<213> ORGANISM: Artificial
<220> FEATURE:
<223> OTHER INFORMATION: Shigella flexneri

<400> SEQUENCE: 10
actcgagctc ccgtcatcat ccaacgc                                   27

<210> SEQ ID NO 11
<211> LENGTH: 29
<212> TYPE: DNA
<213> ORGANISM: Artificial
<220> FEATURE:
<223> OTHER INFORMATION: Shigella flexneri

<400> SEQUENCE: 11
actcgagctc atccgatata cgttcgccc                                 29

<210> SEQ ID NO 12
<211> LENGTH: 31
<212> TYPE: DNA
<213> ORGANISM: Artificial
<220> FEATURE:
<223> OTHER INFORMATION: Shigella flexneri

<400> SEQUENCE: 12
acgcgtcgac ctcagtaatc agggttcttt g                              31

<210> SEQ ID NO 13
<211> LENGTH: 30
<212> TYPE: DNA
<213> ORGANISM: Artificial
<220> FEATURE:
<223> OTHER INFORMATION: Shigella flexneri

<400> SEQUENCE: 13
ctaacccggg taaatctccc ctgccggatg                                30
```

<210> SEQ ID NO 14
<211> LENGTH: 31
<212> TYPE: DNA
<213> ORGANISM: Artificial
<220> FEATURE:
<223> OTHER INFORMATION: Shigella flexneri

<400> SEQUENCE: 14
acgcgtcgac cctgtaatct caggtcaaat g                                    31

<210> SEQ ID NO 15
<211> LENGTH: 30
<212> TYPE: DNA
<213> ORGANISM: Artificial
<220> FEATURE:
<223> OTHER INFORMATION: Shigella flexneri

<400> SEQUENCE: 15
ctaacccggg taaatctccc atgccggatg                                      30

<210> SEQ ID NO 16
<211> LENGTH: 36
<212> TYPE: DNA
<213> ORGANISM: Artificial
<220> FEATURE:
<223> OTHER INFORMATION: Shigella flexneri

<400> SEQUENCE: 16
ctagtctaga aacccgggtg atagtgtagc ggcaca                               36

<210> SEQ ID NO 17
<211> LENGTH: 27
<212> TYPE: DNA
<213> ORGANISM: Artificial
<220> FEATURE:
<223> OTHER INFORMATION: Shigella flexneri

<400> SEQUENCE: 17
actcgagctc gtgagcaaag ccagctg                                         27

<210> SEQ ID NO 18
<211> LENGTH: 27
<212> TYPE: DNA
<213> ORGANISM: Artificial
<220> FEATURE:
<223> OTHER INFORMATION: Shigella flexneri

<400> SEQUENCE: 18
acgcgtcgac ctcggtgtgg aaattgg                                         27

<210> SEQ ID NO 19
<211> LENGTH: 29
<212> TYPE: DNA
<213> ORGANISM: Artificial
<220> FEATURE:
<223> OTHER INFORMATION: Shigella flexneri

<400> SEQUENCE: 19
ctaacccggg caacgtactt actctaccg                                       29

<210> SEQ ID NO 20
<211> LENGTH: 31
<212> TYPE: DNA
<213> ORGANISM: Artificial
<220> FEATURE:
<223> OTHER INFORMATION: Shigella flexneri

```
<400> SEQUENCE: 20
accggaattc gtgtaacact ggcatggtgt a                              31

<210> SEQ ID NO 21
<211> LENGTH: 31
<212> TYPE: DNA
<213> ORGANISM: Artificial
<220> FEATURE:
<223> OTHER INFORMATION: Shigella flexneri

<400> SEQUENCE: 21
catgccattg tagcaatccg ctgttggtgc g                              31

<210> SEQ ID NO 22
<211> LENGTH: 35
<212> TYPE: DNA
<213> ORGANISM: Artificial
<220> FEATURE:
<223> OTHER INFORMATION: Shigella flexneri

<400> SEQUENCE: 22
agcttgatat cagagtgtgt tgatagtgca gtatc                          35

<210> SEQ ID NO 23
<211> LENGTH: 34
<212> TYPE: DNA
<213> ORGANISM: Artificial
<220> FEATURE:
<223> OTHER INFORMATION: Shigella flexneri

<400> SEQUENCE: 23
agcttgatat cacctcttta gcttcttgga agct                           34

<210> SEQ ID NO 24
<211> LENGTH: 31
<212> TYPE: DNA
<213> ORGANISM: Artificial
<220> FEATURE:
<223> OTHER INFORMATION: Shigella flexneri

<400> SEQUENCE: 24
agcttgatat ctgtgacgga agatcacttc g                              31

<210> SEQ ID NO 25
<211> LENGTH: 31
<212> TYPE: DNA
<213> ORGANISM: Artificial
<220> FEATURE:
<223> OTHER INFORMATION: Shigella flexneri

<400> SEQUENCE: 25
agcttgatat cgggcaccaa taactgcctt a                              31

<210> SEQ ID NO 26
<211> LENGTH: 24
<212> TYPE: DNA
<213> ORGANISM: Artificial
<220> FEATURE:
<223> OTHER INFORMATION: Shigella flexneri

<400> SEQUENCE: 26
cggcatcaga ataatacaag cagc                                      24

<210> SEQ ID NO 27
```

```
<211> LENGTH: 19
<212> TYPE: DNA
<213> ORGANISM: Artificial
<220> FEATURE:
<223> OTHER INFORMATION: Shigella flexneri

<400> SEQUENCE: 27
aggtgtaccg tgctctggg                                               19

<210> SEQ ID NO 28
<211> LENGTH: 24
<212> TYPE: DNA
<213> ORGANISM: Artificial
<220> FEATURE:
<223> OTHER INFORMATION: Shigella flexneri

<400> SEQUENCE: 28
gtcacaggta acatgactct ggag                                         24

<210> SEQ ID NO 29
<211> LENGTH: 25
<212> TYPE: DNA
<213> ORGANISM: Artificial
<220> FEATURE:
<223> OTHER INFORMATION: Shigella flexneri

<400> SEQUENCE: 29
ccatgtgtga atactacctt caccc                                        25

<210> SEQ ID NO 30
<211> LENGTH: 25
<212> TYPE: DNA
<213> ORGANISM: Artificial
<220> FEATURE:
<223> OTHER INFORMATION: Shigella flexneri

<400> SEQUENCE: 30
gttttgcctc attcaagata tcacc                                        25

<210> SEQ ID NO 31
<211> LENGTH: 23
<212> TYPE: DNA
<213> ORGANISM: Artificial
<220> FEATURE:
<223> OTHER INFORMATION: Shigella flexneri

<400> SEQUENCE: 31
tgacgatggt ttgtcaggat tgc                                          23

<210> SEQ ID NO 32
<211> LENGTH: 23
<212> TYPE: DNA
<213> ORGANISM: Artificial
<220> FEATURE:
<223> OTHER INFORMATION: Shigella flexneri

<400> SEQUENCE: 32
cgccaaagtt ccgtgatccc att                                          23

<210> SEQ ID NO 33
<211> LENGTH: 23
<212> TYPE: DNA
<213> ORGANISM: Artificial
<220> FEATURE:
<223> OTHER INFORMATION: Shigella flexneri

<400> SEQUENCE: 33
```

-continued ctcttcgatg atctccagcc ctt                          23

<210> SEQ ID NO 34
<211> LENGTH: 23
<212> TYPE: DNA
<213> ORGANISM: Artificial
<220> FEATURE:
<223> OTHER INFORMATION: Shigella flexneri

<400> SEQUENCE: 34
cacgtcttga gcgattgtgt agg                          23

<210> SEQ ID NO 35
<211> LENGTH: 23
<212> TYPE: DNA
<213> ORGANISM: Artificial
<220> FEATURE:
<223> OTHER INFORMATION: Shigella flexneri

<400> SEQUENCE: 35
gacatgggaa ttagccatgg tcc                          23

<210> SEQ ID NO 36
<211> LENGTH: 19
<212> TYPE: DNA
<213> ORGANISM: Artificial
<220> FEATURE:
<223> OTHER INFORMATION: Shigella flexneri

<400> SEQUENCE: 36
caattggtct gttcgccgc                               19

<210> SEQ ID NO 37
<211> LENGTH: 21
<212> TYPE: DNA
<213> ORGANISM: Artificial
<220> FEATURE:
<223> OTHER INFORMATION: Shigella flexneri

<400> SEQUENCE: 37
ctaccgcacc tgaatcaacc a                            21

<210> SEQ ID NO 38
<211> LENGTH: 70
<212> TYPE: DNA
<213> ORGANISM: Artificial
<220> FEATURE:
<223> OTHER INFORMATION: Shigella flexneri

<400> SEQUENCE: 38
accgccaggc gtttaccgtt agcgagagca acaaggggta agccatggcc gtgtaggctg     60
gagctgcttc                                                            70

<210> SEQ ID NO 39
<211> LENGTH: 70
<212> TYPE: DNA
<213> ORGANISM: Artificial
<220> FEATURE:
<223> OTHER INFORMATION: Shigella flexneri

<400> SEQUENCE: 39
acccgctctc tttcaagcaa gggaaacgca gatgtttaga taggctgcgt catatgaata     60
tcctccttag                                                            70

```
<210> SEQ ID NO 40
<211> LENGTH: 70
<212> TYPE: DNA
<213> ORGANISM: Artificial
<220> FEATURE:
<223> OTHER INFORMATION: Shigella flexneri

<400> SEQUENCE: 40
acaatacata caattgcccg tataggttga aaaacaggat tgatatgacg gtgtaggctg    60
gagctgcttc                                                          70

<210> SEQ ID NO 41
<211> LENGTH: 70
<212> TYPE: DNA
<213> ORGANISM: Artificial
<220> FEATURE:
<223> OTHER INFORMATION: Shigella flexneri

<400> SEQUENCE: 41
atgccggatg ccattctgaa gcatccggca tgggagattt aatagcgtga catatgaata    60
tcctccttag                                                          70

<210> SEQ ID NO 42
<211> LENGTH: 70
<212> TYPE: DNA
<213> ORGANISM: Artificial
<220> FEATURE:
<223> OTHER INFORMATION: Shigella flexneri

<400> SEQUENCE: 42
actatcacca gattgatttt tgccttatcc gaaactggaa aagcatggaa gtgtaggctg    60
gagctgcttc                                                          70

<210> SEQ ID NO 43
<211> LENGTH: 70
<212> TYPE: DNA
<213> ORGANISM: Artificial
<220> FEATURE:
<223> OTHER INFORMATION: Shigella flexneri

<400> SEQUENCE: 43
tttattttga tgggataaag atctttgcgc ttatacggct ggatttcgcc catatgaata    60
tcctccttag                                                          70

<210> SEQ ID NO 44
<211> LENGTH: 21
<212> TYPE: DNA
<213> ORGANISM: Artificial
<220> FEATURE:
<223> OTHER INFORMATION: Shigella flexneri

<400> SEQUENCE: 44
cgatagggat gttgccaggt t                                             21

<210> SEQ ID NO 45
<211> LENGTH: 22
<212> TYPE: DNA
<213> ORGANISM: Artificial
<220> FEATURE:
<223> OTHER INFORMATION: Shigella flexneri

<400> SEQUENCE: 45
ctatcggcac gcacctcatt ta                                            22
```

<210> SEQ ID NO 46
<211> LENGTH: 24
<212> TYPE: DNA
<213> ORGANISM: Artificial
<220> FEATURE:
<223> OTHER INFORMATION: Shigella flexneri

<400> SEQUENCE: 46
ctttcccctg tttactggtt taca                                          24

<210> SEQ ID NO 47
<211> LENGTH: 17
<212> TYPE: DNA
<213> ORGANISM: Artificial
<220> FEATURE:
<223> OTHER INFORMATION: Shigella flexneri

<400> SEQUENCE: 47
tgtccgcgct ggcaatg                                                  17

<210> SEQ ID NO 48
<211> LENGTH: 20
<212> TYPE: DNA
<213> ORGANISM: Artificial
<220> FEATURE:
<223> OTHER INFORMATION: Shigella flexneri

<400> SEQUENCE: 48
aacccgcgtc gaactaatcc                                               20

<210> SEQ ID NO 49
<211> LENGTH: 45
<212> TYPE: DNA
<213> ORGANISM: Artificial
<220> FEATURE:
<223> OTHER INFORMATION: Shigella flexneri

<400> SEQUENCE: 49
cctacacaat cgctcaagac gtgcgtttcc atgcttttcc agttt                   45

<210> SEQ ID NO 50
<211> LENGTH: 47
<212> TYPE: DNA
<213> ORGANISM: Artificial
<220> FEATURE:
<223> OTHER INFORMATION: Shigella flexneri

<400> SEQUENCE: 50
ggaccatggc taattcccat gtccccatca aataaaaaag cctctcg                 47

<210> SEQ ID NO 51
<211> LENGTH: 20
<212> TYPE: DNA
<213> ORGANISM: Artificial
<220> FEATURE:
<223> OTHER INFORMATION: Shigella flexneri

<400> SEQUENCE: 51
atcccgagca tcaacgtttc                                               20

<210> SEQ ID NO 52
<211> LENGTH: 19
<212> TYPE: DNA
<213> ORGANISM: Artificial
<220> FEATURE:

<223> OTHER INFORMATION: Shigella flexneri

<400> SEQUENCE: 52
gcgcagtacc cagaaggat                                             19

<210> SEQ ID NO 53
<211> LENGTH: 46
<212> TYPE: DNA
<213> ORGANISM: Artificial
<220> FEATURE:
<223> OTHER INFORMATION: Shigella flexneri

<400> SEQUENCE: 53
cctacacaat cgctcaagac gtgggtggag aacttgggta gattcg                46

<210> SEQ ID NO 54
<211> LENGTH: 46
<212> TYPE: DNA
<213> ORGANISM: Artificial
<220> FEATURE:
<223> OTHER INFORMATION: Shigella flexneri

<400> SEQUENCE: 54
ggaccatggc taattcccat gtcccttcac gctattaaat ctccca                46

<210> SEQ ID NO 55
<211> LENGTH: 22
<212> TYPE: DNA
<213> ORGANISM: Artificial
<220> FEATURE:
<223> OTHER INFORMATION: Shigella flexneri

<400> SEQUENCE: 55
tgactacatc tacaccagcc ct                                          22

<210> SEQ ID NO 56
<211> LENGTH: 20
<212> TYPE: DNA
<213> ORGANISM: Artificial
<220> FEATURE:
<223> OTHER INFORMATION: Shigella flexneri

<400> SEQUENCE: 56
gcgtactttg gttggtcgtg                                             20

<210> SEQ ID NO 57
<211> LENGTH: 18
<212> TYPE: DNA
<213> ORGANISM: Artificial
<220> FEATURE:
<223> OTHER INFORMATION: Shigella flexneri

<400> SEQUENCE: 57
aacgaagggc accagaca                                               18

<210> SEQ ID NO 58
<211> LENGTH: 22
<212> TYPE: DNA
<213> ORGANISM: Artificial
<220> FEATURE:
<223> OTHER INFORMATION: Shigella flexneri

<400> SEQUENCE: 58
ggttatgatg gctacggtgg ta                                          22

```
<210> SEQ ID NO 59
<211> LENGTH: 22
<212> TYPE: DNA
<213> ORGANISM: Artificial
<220> FEATURE:
<223> OTHER INFORMATION: Shigella flexneri

<400> SEQUENCE: 59
gtttatagtc cttctgcgcc ca                                   22

<210> SEQ ID NO 60
<211> LENGTH: 20
<212> TYPE: DNA
<213> ORGANISM: Artificial
<220> FEATURE:
<223> OTHER INFORMATION: Shigella flexneri

<400> SEQUENCE: 60
aacccgcgtc gaactaatcc                                      20

<210> SEQ ID NO 61
<211> LENGTH: 45
<212> TYPE: DNA
<213> ORGANISM: Artificial
<220> FEATURE:
<223> OTHER INFORMATION: Shigella flexneri

<400> SEQUENCE: 61
cctacacaat cgctcaagac gtgcgtttcc atgcttttcc agttt           45

<210> SEQ ID NO 62
<211> LENGTH: 47
<212> TYPE: DNA
<213> ORGANISM: Artificial
<220> FEATURE:
<223> OTHER INFORMATION: Shigella flexneri

<400> SEQUENCE: 62
ggaccatggc taattcccat gtccccatca aataaaaaag cctctcg         47

<210> SEQ ID NO 63
<211> LENGTH: 20
<212> TYPE: DNA
<213> ORGANISM: Artificial
<220> FEATURE:
<223> OTHER INFORMATION: Shigella flexneri

<400> SEQUENCE: 63
atcccgagca tcaacgtttc                                      20

<210> SEQ ID NO 64
<211> LENGTH: 19
<212> TYPE: DNA
<213> ORGANISM: Artificial
<220> FEATURE:
<223> OTHER INFORMATION: Shigella flexneri

<400> SEQUENCE: 64
gcgcagtacc cagaaggat                                       19

<210> SEQ ID NO 65
<211> LENGTH: 46
<212> TYPE: DNA
<213> ORGANISM: Artificial
<220> FEATURE:
<223> OTHER INFORMATION: Shigella flexneri
```

```
<400> SEQUENCE: 65
cctacacaat cgctcaagac gtgggtggag aacttgggta gattcg                          46

<210> SEQ ID NO 66
<211> LENGTH: 46
<212> TYPE: DNA
<213> ORGANISM: Artificial
<220> FEATURE:
<223> OTHER INFORMATION: Shigella flexneri

<400> SEQUENCE: 66
ggaccatggc taattcccat gtcccttcac gctattaaat ctccca                          46

<210> SEQ ID NO 67
<211> LENGTH: 22
<212> TYPE: DNA
<213> ORGANISM: Artificial
<220> FEATURE:
<223> OTHER INFORMATION: Shigella flexneri

<400> SEQUENCE: 67
tgactacatc tacaccagcc ct                                                    22
```